US012575715B2

(12) United States Patent
Nakai

(10) Patent No.: US 12,575,715 B2
(45) Date of Patent: Mar. 17, 2026

(54) FLEXIBLE TUBE FOR ENDOSCOPE, ENDOSCOPIC MEDICAL DEVICE, AND METHODS FOR PRODUCING THE SAME

(71) Applicant: FUJIFILM Corporation, Tokyo (JP)

(72) Inventor: Yoshihiro Nakai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 384 days.

(21) Appl. No.: 18/325,121

(22) Filed: May 30, 2023

(65) Prior Publication Data

US 2023/0301495 A1 Sep. 28, 2023

Related U.S. Application Data

(63) Continuation of application No. PCT/JP2021/043513, filed on Nov. 29, 2021.

(30) Foreign Application Priority Data

Dec. 24, 2020 (JP) ................................. 2020-215763

(51) Int. Cl.
*A61B 1/00* (2006.01)
*A61B 1/005* (2006.01)
(Continued)

(52) U.S. Cl.
CPC ............ *A61B 1/0011* (2013.01); *A61B 1/005* (2013.01); *A61L 29/02* (2013.01); *A61L 29/085* (2013.01);
(Continued)

(58) Field of Classification Search
CPC ..... A61B 1/0011; A61B 1/005; A61L 29/085; A61L 29/146; A61L 2420/02; A61L 2420/06; A61L 2420/08; A61M 25/0045
See application file for complete search history.

(56) References Cited

U.S. PATENT DOCUMENTS 5,677,355 A * 10/1997 Shalaby .............. A61L 27/3852
521/49
5,788,714 A 8/1998 Ouchi
(Continued)

FOREIGN PATENT DOCUMENTS

EP 3653104 5/2020
JP 2006081613 3/2006
(Continued)

OTHER PUBLICATIONS

"Search Report of Europe Counterpart Application", issued on Jan. 24, 2024, p. 1-p. 7.
(Continued)

*Primary Examiner* — Timothy J Neal
(74) *Attorney, Agent, or Firm* — JCIPRNET

(57) ABSTRACT

Provided are a flexible tube for an endoscope, the flexible tube having good elasticity, being capable of sufficiently maintaining adhesiveness between a flexible-tube base and a polymer cover layer covering the flexible-tube base even when a bending operation is repeated, and being less likely to undergo a decrease in elasticity even when the flexible tube is repeatedly heated, an endoscopic medical device including the flexible tube for an endoscope, and methods for producing the flexible tube and the endoscopic medical device.

The flexible tube for an endoscope has a flexible-tube base containing metal as a constituent material, a porous layer on the flexible-tube base, a primer layer on the porous layer, and a polymer cover layer on the primer layer. The polymer cover layer includes at least one compound of a polyamide, a polyester, a polyurethane, or a polyolefin on a side in contact with the primer layer.

14 Claims, 4 Drawing Sheets

(51) Int. Cl.

| | | |
|---|---|---|
| *A61L 29/02* | (2006.01) |
| *A61L 29/08* | (2006.01) |
| *A61L 29/14* | (2006.01) |
| *A61M 25/00* | (2006.01) |

(52) U.S. Cl.

CPC ......... *A61L 29/146* (2013.01); *A61L 2420/02* (2013.01); *A61L 2420/06* (2013.01); *A61L 2420/08* (2013.01); *A61M 25/0045* (2013.01)

(56) References Cited

U.S. PATENT DOCUMENTS

| | | | |
|---|---|---|---|
| 2005/0288545 A1* | 12/2005 | Matsumoto ............ | A61B 1/005 |
| | | | 600/101 |
| 2010/0036201 A1 | 2/2010 | Ogura | |
| 2010/0145151 A1 | 6/2010 | Fukunaga et al. | |
| 2016/0088998 A1 | 3/2016 | Nagai et al. | |
| 2020/0100652 A1* | 4/2020 | Yoshitani ............. | C08K 5/5415 |

FOREIGN PATENT DOCUMENTS

| | | | | |
|---|---|---|---|---|
| JP | 2006081662 | 3/2006 | | |
| JP | 2010035923 | 2/2010 | | |
| JP | 2010136834 | 6/2010 | | |
| JP | 2016067566 | 5/2016 | | |
| WO | WO-2019013243 A1 * | 1/2019 | ........... | C09J 175/06 |

OTHER PUBLICATIONS

"Notice of Reasons for Refusal of Japan Counterpart Application", issued on Apr. 15, 2025, with English translation thereof, p. 1-p. 8.

"Office Action of Japan Counterpart Application", issued on Jul. 1, 2025, with English translation thereof, p. 1-p. 8.

"International Search Report (Form PCT/ISA/210) of PCT/JP2021/043513", mailed on Feb. 15, 2022, with English translation thereof, pp. 1-6.

"Written Opinion of the International Searching Authority (Form PCT/ISA/237) of PCT/JP2021/043513", mailed on Feb. 15, 2022, with English translation thereof, pp. 1-8.

* cited by examiner

FIG. 3

FLEXIBLE TUBE FOR ENDOSCOPE, ENDOSCOPIC MEDICAL DEVICE, AND METHODS FOR PRODUCING THE SAME

CROSS-REFERENCE TO RELATED APPLICATIONS

This application is a Continuation of PCT International Application No. PCT/JP2021/043513 filed on Nov. 29, 2021, which claims priority under 35 U.S.C. § 119 (a) to Japanese Patent Application No. 2020-215763 filed in Japan on Dec. 24, 2020. Each of the above applications is hereby expressly incorporated by reference, in its entirety, into the present application.

BACKGROUND OF THE INVENTION

1. Field of the Invention

The present invention relates to a flexible tube for an endoscope, an endoscopic medical device, and methods for producing the same.

2. Description of the Related Art

Endoscopes are medical devices for examining the inside of the body cavity, the inside of the digestive tract, the esophagus, or the like of a patient. Since endoscopes are inserted and used in the body, it is desirable to provide endoscopes that do not damage organs or cause pain or discomfort to a patient. In view of such a requirement, a spiral tube formed by spirally winding a soft, bendable metal strip is used for a flexible tube constituting an insertion section (structural section to be inserted into the body cavity) of an endoscope. Furthermore, the periphery of the spiral tube is covered with a flexible polymer, and this polymer cover layer is covered with a topcoat layer as required so as not to cause stimulation or damage to the inner surface of, for example, the esophagus, digestive tract, or body cavity.

The flexible tube is required to have high elasticity in order to move smoothly in the body. By increasing elasticity of the flexible tube, the flexible tube that has passed through a bent portion in the body easily returns to a straight shape, and the burden on the subject during the examination can be further reduced. For example, JP2010-035923A discloses, as a technology that meets this requirement, that, after a primer is applied to a surface of a metal core member (flexible-tube base), an outer cover layer is formed to cover the primer, and that a silane coupling agent, a titanate-based coupling agent, an aluminum-based coupling agent, and a zirconium-based coupling agent can be used as the primer. According to JP2010-035923A, this flexible tube for an endoscope has good elasticity.

SUMMARY OF THE INVENTION

Meanwhile, to improve, for example, operability and durability of an endoscope, it is important to enhance adhesiveness between a flexible-tube base and a polymer cover layer that covers the flexible-tube base. If this adhesiveness is insufficient, when a flexible tube is inserted into the body, for example, a crease, lifting, tearing, or separation tends to occur in the polymer cover layer by bending the flexible tube, and when the flexible tube is rotated in the inserted state, twisting of the polymer cover layer tends to occur. If such a crease, lifting, tearing, separation, or twisting occurs in the polymer cover layer, for example, the surface of the flexible tube inserted in the body may catch the surrounding tissues, which may cause a pain to the subject. However, the flexible tube for an endoscope described in JP2010-035923A does not sufficiently meet the requirement for the adhesiveness between the flexible-tube base and the polymer cover layer.

In addition, the endoscope is exposed to heat generated from, for example, an illumination light source housed within the endoscope during use. The endoscope may also be exposed to heat up to about 60° C. during disinfection treatment or sterilization treatment with a chemical solution. As a result of studies conducted by the inventors of the present invention, it has been found that the flexible tube is exposed to a heat cycle by repeatedly using the endoscope, and as a result, the elasticity decreases. Accordingly, the flexible tube for an endoscope is also required to have a property of being less likely to be affected by a heat cycle (i.e., a property of being less likely to undergo a decrease in elasticity even when repeatedly heated).

An object of the present invention is to provide a flexible tube for an endoscope, the flexible tube having good elasticity, being capable of sufficiently maintaining adhesiveness between a flexible-tube base and a polymer cover layer covering the flexible-tube base even when a bending operation is repeated, and being less likely to undergo a decrease in elasticity even when the flexible tube is repeatedly heated, and an endoscopic medical device including the flexible tube for an endoscope. Another object of the present invention is to provide a method for producing the flexible tube for an endoscope and a method for producing the endoscopic medical device.

In view of the above problems, the inventors of the present invention have conducted extensive studies on formation of a polymer cover layer in a flexible tube for an endoscope. As a result, the inventors have found that the objects can be achieved by forming a porous layer on a surface of a flexible-tube base made of a metal material, forming a primer layer on the porous layer, and further using a specific polymer as a constituent material of a polymer cover layer that is in contact with the primer layer. The inventors have further conducted studies on the basis of these findings and completed the present invention.

The above objects of the present invention have been achieved by the following means.

<1>

A flexible tube for an endoscope, the flexible tube having a flexible-tube base containing metal as a constituent material; a porous layer on the flexible-tube base; a primer layer on the porous layer; and a polymer cover layer on the primer layer, wherein the polymer cover layer includes at least one compound of a polyamide, a polyester, a polyurethane, or a polyolefin on a side in contact with the primer layer.

<2>

The flexible tube for an endoscope according to <1>, wherein the porous layer includes a polymer compound, and the porous layer has an average pore size of 50 nm to 100 μm.

<3>

The flexible tube for an endoscope according to <1> or <2>, wherein the primer layer includes at least one of a silane coupling agent, a titanium coupling agent, a zirconium coupling agent, or an aluminum coupling agent.

<4>

The flexible tube for an endoscope according to any one of <1> to <3>, wherein the primer layer includes a silane coupling agent.

<5>

The flexible tube for an endoscope according to any one of <1> to <4>, wherein the primer layer includes an amino silane coupling agent.

<6>

The flexible tube for an endoscope according to any one of <1> to <5>, wherein the metal that constitutes the flexible-tube base is stainless steel.

<7>

The flexible tube for an endoscope according to any one of <1> to <6>, wherein the metal that constitutes the flexible-tube base has a passivation film on a surface of the metal.

<8>

The flexible tube for an endoscope according to any one of <1> to <7>, wherein the polymer cover layer has a single-layer structure or a multilayer structure and includes at least one compound of a polyamide, a polyester, a polyurethane, or a polyolefin in a layer in contact with the primer layer.

<9>

The flexible tube for an endoscope according to any one of <1> to <8>, wherein the polymer cover layer has a two-layer structure, and a proportion of a thickness of an inner layer to a thickness of an outer layer of the two-layer structure changes in a gradient manner in an axial direction of the flexible-tube base.

<10>

The flexible tube for an endoscope according to any one of <1> to <9>, wherein the proportion of the thickness of the inner layer to the thickness of the outer layer is inner layer:outer layer=95:5 to 60:40 at one end of the flexible tube for an endoscope and is inner layer:outer layer=5:95 to 40:60 at the other end.

<11>

An endoscopic medical device having the flexible tube for an endoscope according to any one of <1> to <10>.

<12>

A method for producing a flexible tube for an endoscope, the method including forming, on a flexible-tube base containing metal as a constituent material, a porous layer having an average pore size of 50 nm to 100 μm; forming a primer layer on the porous layer; and forming a polymer cover layer on the primer layer, wherein the polymer cover layer includes at least one compound of a polyamide, a polyester, a polyurethane, or a polyolefin on a side in contact with the primer layer.

<13>

A method for producing an endoscopic medical device, the method including incorporating, into an insertion section of an endoscopic medical device, a flexible tube for an endoscope obtained by the method for producing a flexible tube for an endoscope according to <12>.

<14>

A method for producing an endoscopic medical device, the method including incorporating, into an insertion section of an endoscopic medical device, the flexible tube for an endoscope according to any one of <1> to <10>.

In the present specification, when a plurality of substituents, linking groups, or the like (hereinafter referred to as substituents or the like) represented by specific symbols are present or a plurality of sub stituents or the like are defined simultaneously or alternatively, the substituents or the like may be the same or different from each other. In addition, even if not specifically stated, when a plurality of substituents or the like are adjacent to each other, they may be linked or fused to each other to form a ring.

In the present specification, a substituent for which substitution or non-substitution is not specified (the same applies to a linking group) means that the group may have any substituent as long as the desired effect is achieved. The same applies to a compound for which substitution or non-substitution is not specified.

In the present specification, when the number of carbon atoms of a group is specified, the number of carbon atoms means the number of carbon atoms of the whole group. That is, when this group has a form further having a substituent, the number of carbon atoms means the number of carbon atoms of the whole structure that includes this substituent.

The flexible tube for an endoscope according to the present invention has good elasticity, can sufficiently maintain adhesiveness between a flexible-tube base and a polymer cover layer covering the flexible-tube base even when a bending operation is repeated, and is less likely to undergo a decrease in elasticity even when the flexible tube is exposed to a heat cycle by repeatedly using the endoscope.

In the endoscopic medical device according to the present invention, a flexible tube, which is a structural section to be inserted into the body, has good elasticity, can sufficiently maintain adhesiveness between a flexible-tube base and a polymer cover layer covering the flexible-tube base even when a bending operation is repeated, and is less likely to undergo a decrease in elasticity even when the flexible tube is exposed to a heat cycle due to repeated use. Accordingly, the endoscopic medical device according to the present invention has good durability and can further reduce the burden on the subject during use.

The method for producing a flexible tube for an endoscope according to the present invention can provide a flexible tube for an endoscope, the flexible tube having good elasticity, being capable of sufficiently maintaining adhesiveness between a flexible-tube base and a polymer cover layer covering the flexible-tube base even when a bending operation is repeated, and being less likely to undergo a decrease in elasticity even when the flexible tube is exposed to a heat cycle by repeatedly using the endoscope.

According to the method for producing an endoscopic medical device according to the present invention, a flexible tube constituting the device can have good elasticity and have properties of sufficiently maintaining adhesiveness between a flexible-tube base and a polymer cover layer covering the flexible-tube base even when a bending operation is repeated and being less likely to undergo a decrease in elasticity even when the flexible tube is exposed to a heat cycle by repeatedly using the endoscope. Accordingly, the method for producing an endoscopic medical device according to the present invention can provide an endoscopic medical device that has good durability and that further reduces the burden on the subject during use.

BRIEF DESCRIPTION OF THE DRAWINGS

FIG. 3 is a block diagram illustrating the configuration of an apparatus for producing a flexible tube for an endoscope according to an embodiment.

DESCRIPTION OF THE PREFERRED EMBODIMENTS

Figure 1:
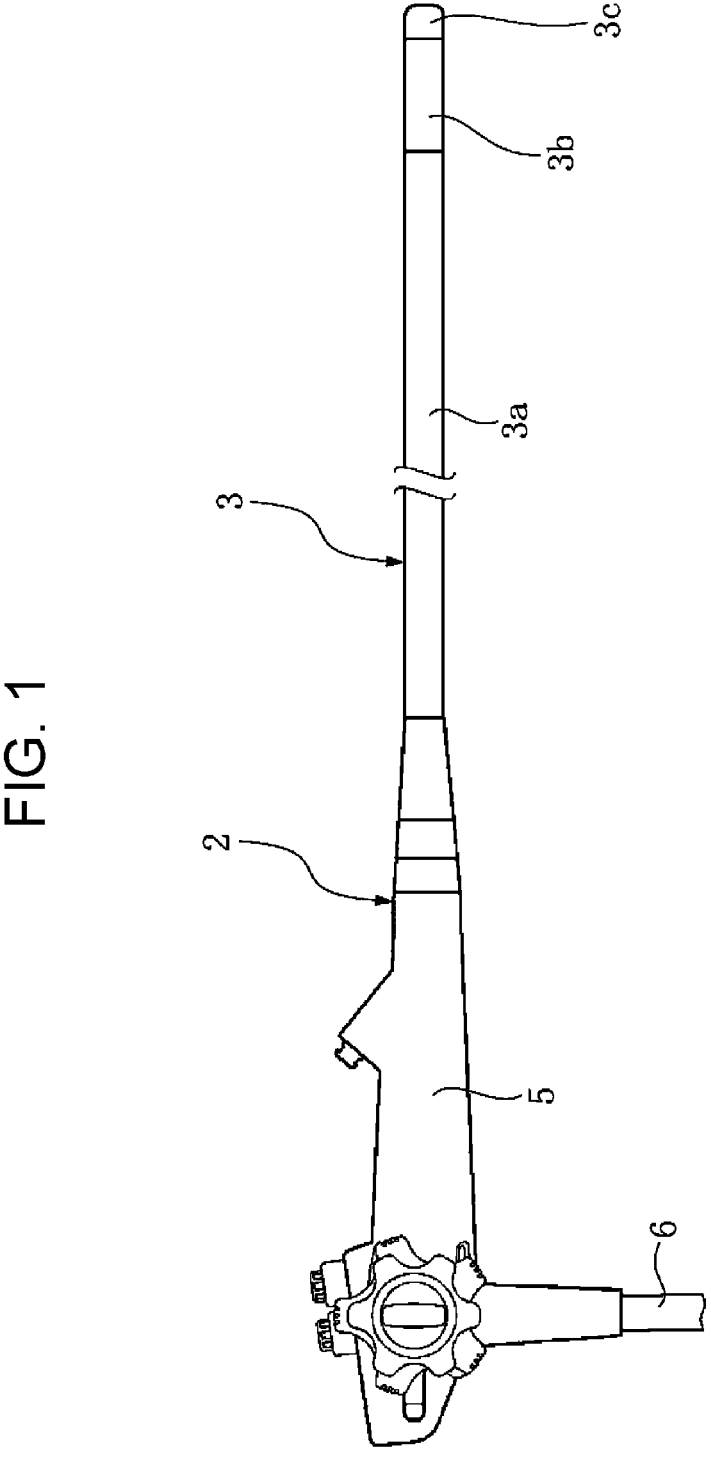
FIG. 1 is an external view illustrating the configuration of an electronic endoscope according to an embodiment.

A preferred embodiment of an endoscopic medical device in which a flexible tube for an endoscope (hereinafter, the flexible tube for an endoscope may be simply referred to as a "flexible tube") according to the present invention is incorporated will be described by taking an electronic endoscope as an example. The electronic endoscope is used as a medical device for, for example, observing the inside of the body by inserting the flexible tube into the body cavity, the digestive tract, the esophagus, or the like. In an example illustrated in FIG. 1, an electronic endoscope 2 includes an insertion section 3 to be inserted into the body, a main-body operation section 5 connected to a proximal end portion of the insertion section 3, and a universal cord 6 to be connected to a processor device or a light source device. The insertion section 3 is constituted by a flexible tube 3*a* connected to the main-body operation section 5, an angle portion 3*b* connected to the flexible tube 3*a*, and a tip portion 3*c* connected to the distal end of the angle portion 3*b* and including therein an imaging device (not illustrated) for capturing an image of the inside of the body. The flexible tube 3*a*, which accounts for most of the length of the insertion section 3, has flexibility across substantially the entire length thereof and is configured so that, in particular, a portion to be inserted into the inside of the body cavity or the like has higher flexibility. In FIG. 1, the angle portion 3*b* side has a soft structure (soft), and the main-body operation section 5 side has a hard structure (hard).

Flexible Tube for Endoscope

A flexible tube for an endoscope according to the present invention has a flexible-tube base containing metal as a constituent material, a porous layer on the flexible-tube base, a primer layer on the porous layer, and a polymer cover layer on the primer layer, in which the polymer cover layer includes at least one compound of a polyamide, a polyester, a polyurethane, or a polyolefin on a side in contact with the primer layer. That is, the flexible tube for an endoscope has a flexible-tube base containing metal as a constituent material, a porous layer, a primer layer, and a polymer cover layer in this order, in which the polymer cover layer includes at least one compound selected from the group consisting of polyamides, polyesters, polyurethanes, and polyolefins on a side in contact with the primer layer.

Figure 2:
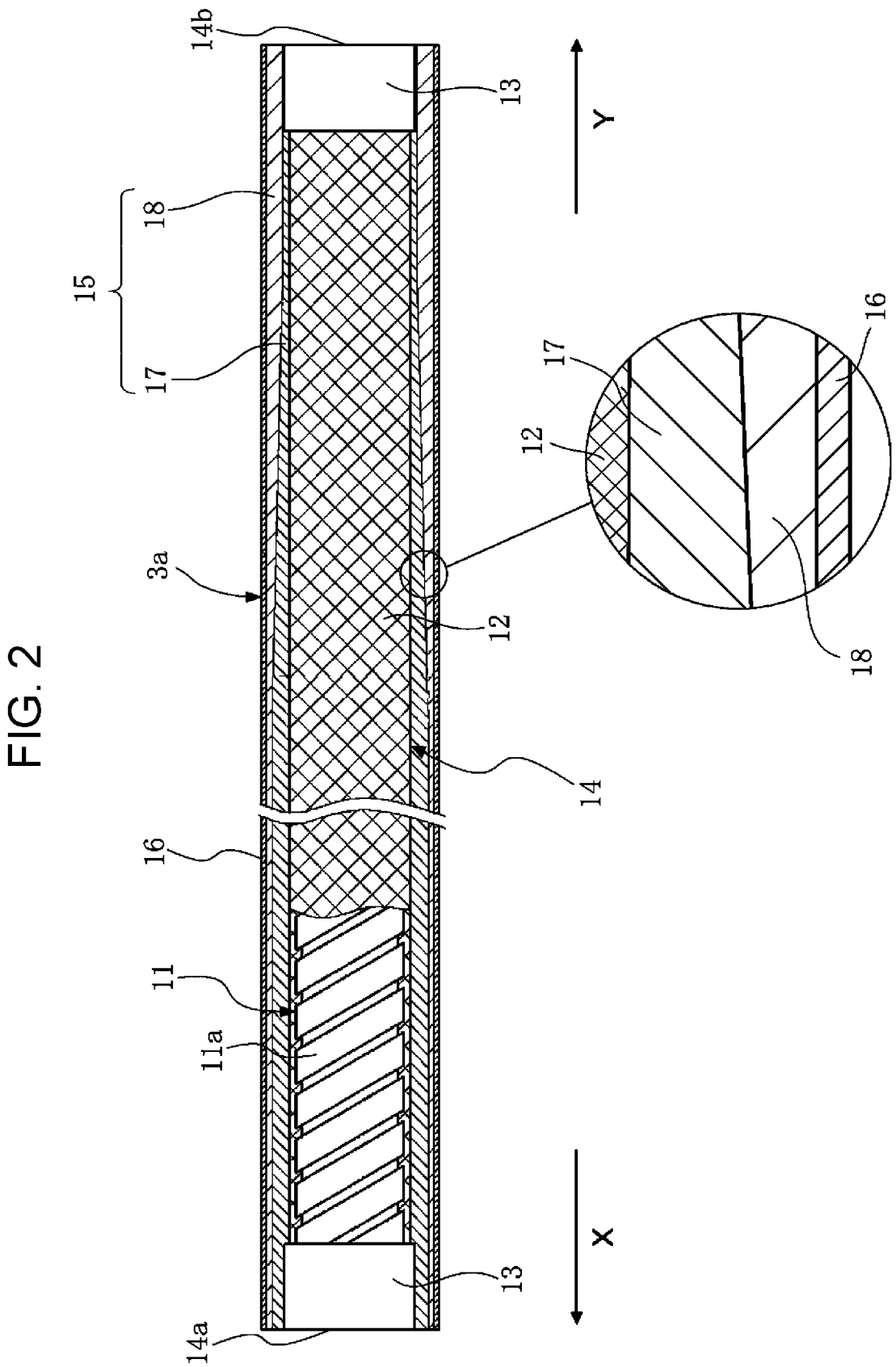
FIG. 2 is a partial sectional view illustrating the configuration of a flexible tube for an endoscope according to an embodiment.

In FIG. 2, the porous layer and the primer layer are not illustrated.

The flexible tube for an endoscope according to the present invention has good elasticity, can sufficiently maintain adhesiveness between a flexible-tube base and a polymer cover layer covering the flexible-tube base even when a bending operation is repeated, and is less likely to undergo a decrease in elasticity even when the flexible tube is repeatedly heated. Although the reason for this is not clear, it is assumed that one of the causes is an anchoring effect by which the polymer cover layer enters pores of the porous layer in a state of being in close contact with the primer layer.

Flexible-Tube Base

The flexible tube has, as an innermost layer, a flexible-tube base containing metal as a constituent material.

As illustrated in FIG. 2, a flexible-tube base 14 preferably has a form in which a spiral tube 11 disposed on the innermost side and formed by spirally winding a metal strip 11*a* is covered with a tubular mesh member 12 formed by weaving metal wires, and caps 13 are fitted to both ends of the flexible-tube base 14. The metal that constitutes the flexible-tube base 14 preferably has a surface that has been subjected to passivation treatment in order to prevent corrosion. That is, the flexible-tube base 14 preferably has a passivation film (for example, a metal oxide film) on the outer periphery thereof. This passivation treatment can be performed by an ordinary method. A passivation film can be formed on a surface of metal by, for example, immersing the metal in a solution including a strong oxidizing agent such as nitric acid, heating the metal in air (oxygen) or water (water vapor), or anodizing the metal in a solution including an oxidizing agent.

The metal that constitutes the flexible-tube base 14 is preferably stainless steel. The surface of stainless steel is usually in a state in which chromium and oxygen are bound together to form a passivation film. However, even when stainless steel is used as the constituent material of the flexible-tube base 14, the stainless steel is preferably subjected to the passivation treatment described above in order to more reliably form a more uniform passivation film over the entire surface of the stainless steel.

Porous Layer

The porous layer that constitutes the flexible tube according to the present invention has a large number of pores (holes) in the layer. Examples of the shapes of the pores include a spherical shape and an ellipsoidal shape. The pores may be independent pores or continuous pores formed by a series of independent pores.

An average pore size of the porous layer is not particularly limited and is, for example, preferably 50 nm to 300 μm, more preferably 70 nm to 100 μm, still more preferably 150 nm to 100 μm, still more preferably 300 nm to 25 μm, still more preferably 450 nm to 25 μm, and still more preferably 450 nm to 5 μm from the viewpoint of elasticity, adhesiveness, and heat resistance. In the specification of this application, the average pore size is a value determined by the method described in Examples below.

A porosity of the porous layer is not particularly limited and is, for example, preferably 10% to 80%, more preferably 20% to 60%, and still more preferably 30% to 50%. In the specification of this application, the "porosity" refers to a ratio of the volume of pores to the volume of the entire porous layer including the pores and is a value determined by the method described in Examples below.

An average layer thickness of the porous layer is not particularly limited and is, for example, preferably 0.01 to 1,000 μm, more preferably 0.05 to 500 μm, and still more preferably 0.1 to 50 μm. In the specification of this application, the average layer thickness is a value determined by the method described in Examples below.

The porous layer preferably includes a polymer compound. Examples of the polymer compound include crosslinked products of epoxy resins, siloxanes (polysiloxanes), vinyl resins (such as acrylic resins and styrene resins), and condensation resins (such as polyamides, polyesters, and polycarbonates), and one or two or more of these can be used. Of these, at least one of a crosslinked product of an epoxy resin or a siloxane is preferred, and a crosslinked product of an epoxy resin is more preferred.

The content of the polymer compound in the porous layer is not particularly limited and is, for example, preferably 80% by mass or more, and more preferably 90% by mass or more. The porous layer may be a layer composed of a polymer compound (polymer compound layer having pores).

The porous layer may include, in addition to the polymer compound, for example, plasticizers, flame retardants, reinforcing agents (e.g., an inorganic filler and a metal filler), and stabilizers such as an antioxidant, as long as the effects of the present invention are not impaired.

As a porous layer including a crosslinked product of an epoxy resin (hereinafter also referred to as a "porous epoxy resin layer"), for example, porous epoxy resin films described in JP2010-77358A and JP2013-18966A may be applied to the porous layer that constitutes the flexible tube according to the present invention.

As a porous layer including a siloxane (hereinafter, also referred to as a "porous silica layer"), for example, a porous silica-based film described in JP2010-64932A, mesoporous silica thin films described in WO2003/028097A and WO2003/075335A, a porous silica film described in JP2003-115486A, a porous silica film described in JP2005-202240A, and a porous silica film described in JP2003-268356A may be applied to the porous layer that constitutes the flexible tube according to the present invention.

Primer Layer

The primer layer that constitutes the flexible tube according to the present invention preferably includes at least one of a silane coupling agent, a titanium coupling agent, a zirconium coupling agent, or an aluminum coupling agent from the viewpoint of elasticity of the flexible tube, adhesiveness between the flexible-tube base and the polymer cover layer, and heat resistance of the flexible tube.

As the silane coupling agent, the titanium coupling agent, the zirconium coupling agent, and the aluminum coupling agent used in the present invention, typical silane coupling agents, titanium coupling agents, zirconium coupling agents and aluminum coupling agents applicable to a primer layer of a flexible tube for an endoscope can be widely used. In the present invention, a silane coupling agent is preferred, and an amino silane coupling agent (preferably a silane coupling agent having at least one of an unsubstituted amino group or a monosubstituted amino group) is more preferred from the viewpoint of elasticity of the flexible tube, adhesiveness between the flexible-tube base and the polymer cover layer, and heat resistance of the flexible tube. Specific examples of the silane coupling agent, the titanium coupling agent, the zirconium coupling agent, and the aluminum coupling agent include silane coupling agents, titanium coupling agents, zirconium coupling agents, and aluminum coupling agents used in Examples described later, but the present invention is not limited to these.

The content of the silane coupling agent, the titanium coupling agent, the zirconium coupling agent, and the aluminum coupling agent in the primer layer is preferably 50% by mass or more, more preferably 70% by mass or more, still more preferably 80% by mass or more, and even more preferably 90% by mass or more, in total. The primer layer may be a layer composed of at least one of a silane coupling agent, a titanium coupling agent, a zirconium coupling agent, or an aluminum coupling agent.

The content of the amino silane coupling agent in the silane coupling agent is preferably 50% by mass or more, more preferably 70% by mass or more, still more preferably 80% by mass or more, and even more preferably 90% by mass or more.

The primer layer may include components other than the silane coupling agent, the titanium coupling agent, the zirconium coupling agent, and the aluminum coupling agent as long as the effects of the present invention are not impaired. Examples of such components include metal alkoxides other than the above coupling agents, binder resins, and stabilizers (for example, surfactants and antioxidants).

In the present invention, "the primer layer includes at least one of a silane coupling agent, a titanium coupling agent, a zirconium coupling agent, or an aluminum coupling agent" is meant to include a form in which at least one of a silane coupling agent, a titanium coupling agent, a zirconium coupling agent, or an aluminum coupling agent is included in a state of having reacted with the porous layer or the flexible-tube base, and a form in which at least one of a silane coupling agent, a titanium coupling agent, a zirconium coupling agent, or an aluminum coupling agent is included in a state of having reacted with the polymer cover layer. For example, a silane coupling agent, a titanium coupling agent, a zirconium coupling agent, and an aluminum coupling agent are at least partially hydrolyzed to expose hydroxy groups, and the coupling agents can be present in a state where the hydroxy groups have reacted with the porous layer or metal constituting the flexible-tube base or have reacted with groups on the surface of the polymer cover layer.

The layer thickness of the primer layer is much smaller than that of a common adhesive layer and is not limited, but is preferably 1 nm or more and 100 nm or less. That is, the primer layer differs from the adhesive layer that requires a certain layer thickness and softness for adhesion between the flexible-tube base and the polymer cover layer.

Polymer Cover Layer

The flexible tube according to the present invention has a polymer cover layer on the outer periphery of the flexible-tube base on which the porous layer and the primer layer are disposed in this order.

In the embodiment in FIG. 2, an outer surface of a polymer cover layer 15 is coated with a topcoat layer 16 that contains fluorine or the like and that contributes to, for example, chemical resistance. In FIG. 2, only a single layer of the spiral tube 11 is illustrated, but the spiral tube 11 may be formed by concentrically stacking two or more layers. Note that the polymer cover layer 15 and the topcoat layer 16 in the drawing are drawn to be thicker than the actual thicknesses with respect to the diameter of the flexible-tube base 14 for the sake of clearly illustrating the layer structure.

In the present invention, the polymer cover layer covers the outer peripheral surface of the flexible-tube base having the porous layer and the primer layer described above. The polymer cover layer 15 in the embodiment in FIG. 2 has a two-layer structure in which an inner layer 17 that covers the entire peripheral surface around the axis of the flexible-tube base 14 and an outer layer 18 that covers the entire peripheral surface around the axis of the inner layer 17 are laminated. Typically, a soft polymer is used as the material of the inner layer 17 and a hard polymer is used as the material of the outer layer 18, but the present invention is not limited to these embodiments.

In the present invention, as described later, when the polymer cover layer has a multilayer structure of two or more layers, at least the innermost layer (layer in contact with the primer layer) includes at least one compound of a polyamide, a polyester, a polyurethane, or a polyolefin. In the present invention, when the polymer cover layer is formed of a single layer, the single-layer polymer cover layer includes at least one compound of a polyamide, a polyester, a polyurethane, or a polyolefin. Specifically, the polymer cover layer in the present invention includes at least one compound of a polyamide, a polyester, a polyurethane, or a polyolefin on at least the side in contact with the primer layer and preferably includes at least one compound of a polyamide, a polyester, or a polyurethane on the side in contact with the primer layer.

Polyamide

Typical polyamides applicable to a polymer cover layer of a flexible tube for an endoscope can be widely used as the polyamides. Examples thereof include crystalline polyamides, amorphous polyamides, and polyamide elastomers.

Examples of the crystalline polyamides include, but are not particularly limited to, aliphatic polyamides and aromatic polyamides.

Examples of the aliphatic polyamides include poly-ε-caproamide (polyamide 6), polytetramethylene adipamide (polyamide 46), polyhexamethylene adipamide (polyamide 66), polycaproamide/polyhexamethylene adipamide copolymers (polyamide 6/66), polyundecamide (polyamide 11), polycaproamide/polyundecamide copolymers (polyamide 6/11), polydodecamide (polyamide 12), polycaproamide/polydodecamide copolymers (polyamide 6/12), polyhexamethylene sebacamide (polyamide 610), polydecamethylene sebacamide (polyamide 1010), polyhexamethylene dodecamide (polyamide 612), polydecamethylene dodecamide (polyamide 1012), polyundecamethylene adipamide (polyamide 116), and mixtures and copolymers thereof.

Examples of the aromatic polyamides include polyhexamethylene isophthalamide (polyamide 6I), polyhexamethylene terephthalamide (polyamide 6T), polyhexamethylene terephthalamide/polyhexamethylene isophthalamide copolymers (polyamide 6T/6I), polycaproamide/polyhexamethylene terephthalamide copolymers (polyamide 6/6T), polycaproamide/polyhexamethylene isophthalamide copolymers (polyamide 6/6I), polyhexamethylene adipamide/polyhexamethylene terephthalamide copolymers (polyamide 66/6T), polyhexamethylene adipamide/polyhexamethylene isophthalamide copolymers (polyamide 66/6I), polytrimethylhexamethylene terephthalamide (polyamide TMDT), polybis(4-aminocyclohexyl)methane dodecamide (polyamide PACM12), polybis(3-methyl-4-aminocyclohexyl)methane dodecamide (nylon dimethyl PACM12), poly-m-xylylene adipamide (polyamide MXD6), polydecamethylene terephthalamide (polyamide 10T), polyundecamethylene terephthalamide (polyamide 11T), and mixtures and copolymers thereof.

Examples of the amorphous polyamides include polycondensates of isophthalic acid/terephthalic acid/1,6-hexanediamine/bis(3-methyl-4-aminocyclohexyl)methane, polycondensates of terephthalic acid/2,2,4-trimethyl-1,6-hexanediamine/2,4,4-trimethyl-1,6-hexanediamine, polycondensates of isophthalic acid/bis(3-methyl-4-aminocyclohexyl)methane/ω-laurolactam, polycondensates of isophthalic acid/terephthalic acid/1,6-hexanediamine, polycondensates of isophthalic acid/2,2,4-trimethyl-1,6-hexanediamine/2,4,4-trimethyl-1,6-hexanediamine, polycondensates of isophthalic acid/terephthalic acid/2,2,4-trimethyl-1,6-hexanediamine/2,4,4-trimethyl-1,6-hexanediamine, polycondensates of isophthalic acid/bis(3-methyl-4-aminocyclohexyl)methane/ω-laurolactam, and polycondensates of isophthalic acid/terephthalic acid/other diamine components.

Examples of the polyamide elastomers include elastomers containing polyamides as hard segments, the elastomers being called amide-based thermoplastic elastomers. Examples thereof include multiblock copolymers having hard segments composed of polyamides and soft segments composed of polyethers or polyesters, and multiblock copolymers having hard segments composed of polyamides and soft segments having bonding forms of both an ether bond and an ester bond. Examples of the hard segments include polyamides 6, 66, 610, 11, and 12. Examples of the polyethers for the soft segments include polyethylene glycol, poly(oxytetramethylene) glycol, and poly(oxypropylene) glycol, and examples of the polyesters include poly(ethylene adipate) glycol and poly(butylene-1,4-adipate) glycol.

Examples of commercially available polyamides that can be used in the present invention include polyamide 11 (trade name "Rilsan BMN O" manufactured by Arkema Inc.), polyamide 12 (trade name "DAIAMID L1940" manufactured by Daicel-Evonik Ltd.), polyamide 1010 (trade name "VESTAMID Terra DS16" manufactured by Daicel-Evonik Ltd.), polyamide 1012 (trade name "VESTAMID Terra DD16" manufactured by Evonik), an amorphous polyamide (trade name "TROGAMID CX7323" manufactured by Daicel-Evonik Ltd.), and polyamide elastomers (trade names "Pebax 4533", "Pebax 7233", and "Pebax Rnew 80R53" manufactured by Arkema Inc.).

These polyamides may be used alone or in combination of two or more thereof.

Polyester

Typical polyesters applicable to a polymer cover layer of a flexible tube for an endoscope can be widely used as the polyesters. Examples thereof include thermoplastic polyesters and polyester elastomers.

Examples of the thermoplastic polyesters include polyester resins formed from a dicarboxylic acid component and a diol component and polyester resins formed from a hydroxycarboxylic acid component.

Examples of the dicarboxylic acid component include terephthalic acid, isophthalic acid, phthalic acid, 2,6-naphthalenedicarboxylic acid, 4,4'-biphenyldicarboxylic acid, sodium 5-sulfoisophthalate, oxalic acid, succinic acid, adipic acid, sebacic acid, azelaic acid, dodecanedioic acid, dimer acids, maleic anhydride, maleic acid, fumaric acid, itaconic acid, citraconic acid, mesaconic acid, and cyclohexanedicarboxylic acid.

Examples of the diol component include ethylene glycol, diethylene glycol, 1,3-propanediol, 1,4-butanediol, neopentyl glycol, 1,6-hexanediol, cyclohexanedimethanol, triethylene glycol, polyethylene glycol, polypropylene glycol, polytetramethylene glycol, and ethylene oxide adducts of bisphenol A and bisphenol S.

Examples of the hydroxycarboxylic acid component include ε-caprolactone, lactic acid, and 4-hydroxybenzoic acid.

The thermoplastic polyesters may be homopolymers formed from the dicarboxylic acid component and the diol component or homopolymers formed from the hydroxycarboxylic acid component, or copolymers formed from the above components. The thermoplastic polyesters may further contain a small amount of a trifunctional or higher compound component such as trimellitic acid, trimesic acid, pyromellitic acid, trimethylolpropane, glycerin, or pentaerythritol.

Examples of the polyester elastomers include elastomers containing polyesters as hard segments, the elastomers being called ester-based thermoplastic elastomers. Examples thereof include multiblock copolymers having hard segments composed of crystalline polyesters and soft segments composed of polyethers or polyesters, and multiblock copolymers having hard segments composed of crystalline polyesters and soft segments having bonding forms of both an ether bond and an ester bond.

Examples of the hard segments include polybutylene terephthalate and polyethylene terephthalate.

Examples of the soft segments include polyalkylene glycols such as polytetramethylene glycol and polypropylene glycol, bisphenol A-ethylene oxide adducts, bisphenol A-propylene oxide adducts, and polyesters such as polycaprolactone.

For example, block copolymers composed of high-melting-point polyester segments (hard segments) and low-melting-point polymer segments (soft segments) having a molecular weight of 400 to 6,000 can be used as the polyester elastomers, as described in, for example, JP1999-92636A (JP-H11-92636A).

Examples of commercially available polyesters used in the present invention include polyester elastomers (trade names "PELPRENE P-40B", "PELPRENE P-70B", and "PELPRENE S-3001" manufactured by Toyobo Co., Ltd. and trade name "PRIMALLOY B1942" manufactured by Mitsubishi Chemical Corporation) and polybutylene terephthalate (trade name "NOVADURAN 5505S" manufactured by Mitsubishi Engineering-Plastics Corporation).

These polyesters may be used alone or in combination of two or more thereof.

Polyurethane

Typical polyurethanes applicable to a polymer cover layer of a flexible tube for an endoscope can be widely used as the polyurethanes. For example, carbonate-based, ether-based, or ester-based polyurethanes, or mixed polyurethanes of these can be used. Polyurethane elastomers are also preferred. The polyurethane elastomers may be block polymers including hard segments composed of polyurethanes and soft segments having an ether, ester, or carbonate bond or a mixed form of these bonds, the block polymers being called urethane-based thermoplastic elastomers. Such polyurethane elastomers can be appropriately prepared depending on the purpose. Examples thereof include block polymers including hard segments composed of low-molecular-weight glycol components and diisocyanate components and soft segments composed of high-molecular-weight (long-chain) diol components and diisocyanate components.

Examples of the high-molecular-weight (long-chain) diol components include polyether diols, polyester diols, and lactone-based polyester diols. Examples thereof include polypropylene glycol, polytetramethylene oxide, poly(1,4-butylene adipate), poly(ethylene adipate-co-1,4-butylene adipate), polycaprolactone-based diol, poly(1,6-hexylene carbonate), and poly(1,6-hexylene adipate-co-neopentylene adipate). The high-molecular-weight (long-chain) diols preferably have a number-average molecular weight of 500 to 10,000.

As the low-molecular-weight glycol components, short-chain diols such as ethylene glycol, propylene glycol, 1,4-butanediol, and bisphenol A can be used. The short-chain diols preferably have a number-average molecular weight of 48 to 500.

Examples of the diisocyanate components include diphenylmethane diisocyanate, hexamethylene diisocyanate, tolidine diisocyanate, 1,5-naphthalene diisocyanate, isophorone diisocyanate, and xylylene diisocyanate.

For the polyurethane elastomers according to the above embodiment, the disclosure of, for example, JP2005-015643A can be referred to.

Examples of commercially available polyurethanes that can be used in the present invention include PANDEX T-2185 and T-2983N (which are manufactured by DIC Corporation), Miractran (manufactured by Nippon Miractran Co., Ltd.), PANDEX (manufactured by DIC Corporation), Elastollan (manufactured by BASF Japan Ltd.), RESAMINE (manufactured by Dainichiseika Color &

Chemicals Mfg. Co., Ltd.), Pellethane (manufactured by Dow Chemical Japan Ltd.), Iron Rubber (manufactured by NOK Corporation), and Mobilon (manufactured by Nisshinbo Chemical Inc.). Examples thereof further include Isoplast (manufactured by Lubrizol Corporation), Tecoflex (manufactured by Lubrizol Corporation), Superflex 830, 460, 870, 420, and 420NS (polyurethanes manufactured by DKS Co., Ltd.), Hydran AP-40F, WLS-202, and HW-140SF (polyurethanes manufactured by DIC Corporation), Olester UD500 and UD350 (polyurethanes manufactured by Mitsui Chemicals, Inc.), and Takelac W-615, W-6010, W-6020, W-6061, W-405, W-5030, W-5661, W-512A-6, W-635, and WPB-6601 (manufactured by Mitsui Chemicals, Inc).

These polyurethanes may be used alone or in combination of two or more thereof.

Polyolefin

Typical polyolefins applicable to a polymer cover layer of a flexible tube for an endoscope can be widely used as the polyolefins. Examples thereof include polyolefin resins and olefin-based elastomers.

Examples of the polyolefin resins and rubbers include homopolymers and copolymers of $\alpha$-olefins having 2 to 20 carbon atoms, such as ethylene, propylene, 1-butene, 1-hexene, and 4-methyl-pentene. Examples thereof further include copolymers of $\alpha$-olefins and nonconjugated dienes having 2 to 20 carbon atoms, such as dicyclopentadiene, 1,4-hexadiene, cyclooctadiene, methylene norbornene, ethylidene norbornene, butadiene, and isoprene. Examples thereof further include ethylene-$\alpha$-olefin copolymer rubbers, ethylene-$\alpha$-olefin-nonconjugated diene copolymer rubbers, propylene-$\alpha$-olefin copolymer rubbers, and butene-$\alpha$-olefin copolymer rubbers. It is also possible to use, for example, ethylene-(meth)acrylic acid copolymers, ethylene-(meth) acrylic acid ester-(meth)acrylic acid copolymers, ethylene-vinyl acetate copolymers, ethylene-vinyl acetate-(meth) acrylic acid copolymers, ethylene-propylene-(meth)acrylic acid copolymers, ethylene-propylene-(meth)acrylic acid ester-(meth)acrylic acid copolymers, ethylene-maleic anhydride copolymers, ethylene-(meth)acrylic acid ester-maleic anhydride copolymers, ethylene-butene-maleic anhydride copolymers, ethylene-butene-(meth)acrylic acid copolymers, ethylene-butene-maleic anhydride-(meth)acrylic acid copolymers, propylene-butene-maleic anhydride copolymers, propylene-butene-(meth)acrylic acid copolymers, propylene-butene-maleic anhydride-(meth)acrylic acid copolymers, ethylene-vinyl chloride copolymers, and ethylene-vinyl chloride copolymers.

Examples of polyolefins in the olefin-based elastomers include ethylene-propylene copolymers, ethylene-1-butene copolymers, ethylene-$\alpha$-olefin copolymers, propylene-1-butene copolymers, propylene-$\alpha$-olefin copolymers, 1-butene-$\alpha$-olefin copolymers, propylene-1-butene-ethylene copolymers, propylene-$\alpha$-olefin-ethylene copolymers, propylene-$\alpha$-olefin-1-butene copolymers, 1-butene-$\alpha$-olefin-ethylene copolymers, and polypropylene.

Examples of rubber components in the olefin-based elastomers include propylene rubber (PP), ethylene-propylene rubber (EPM), ethylene-propylene-diene rubber (EPDM), polyisoprene, polybutadiene, polychloroprene, and isobutylene-isoprene copolymers.

The olefin-based elastomers may contain one of the polyolefins alone or two or more of the polyolefins and may contain one of the rubber components alone or two or more of the rubber components.

Examples of commercially available polyolefins used in the present invention include "SARLINK 3145D" (trade name, manufactured by Toyobo Co., Ltd.) and Zelas MC707 (trade name, manufactured by Mitsubishi Chemical Corporation).

These polyolefins may be used alone or in combination of two or more thereof.

The total amount of compounds selected from the group consisting of polyamides, polyesters, polyurethanes, and polyolefins contained in the polymer cover layer in the case of a single-layer polymer cover layer, and the total amount of compounds selected from the group consisting of polyamides, polyesters, polyurethanes, and polyolefins contained in the innermost layer in the case of a multilayer polymer cover layer are each preferably 50% by mass or more, more preferably 70% by mass or more, still more preferably 80% by mass or more, and even more preferably 90% by mass or more. When the polymer cover layer is formed of a single layer, the polymer cover layer may be a layer composed of at least one compound of a polyamide, a polyester, a polyurethane, or a polyolefin. When the polymer cover layer is formed of a plurality of layers, the innermost layer may be a layer composed of at least one compound of a polyamide, a polyester, a polyurethane, or a polyolefin.

When the polymer cover layer in the case of a single-layer polymer cover layer and the innermost layer in the case of a multilayer polymer cover layer include a polymer other than polymers selected from the group consisting of polyamides, polyesters, polyurethanes, and polyolefins, the polymer is not particularly limited as long as the effects of the present invention are not impaired.

The polymer cover layer may appropriately contain various common additives as long as the effects of the present invention are not impaired. Examples of the additives include a heat-resistant stabilizer, a mineral filler, an impact resistance-improving agent, a plasticizer, a lubricant, a metal soap, a light-fast auxiliary agent, and a colorant. The amounts of the additives contained in the polymer cover layer can also be appropriately adjusted. Such additives may be derived from polymer materials used or can be added separately from polymers.

When the polymer cover layer is formed of a plurality of layers, a layer other than the innermost layer also preferably includes at least one compound of a polyamide, a polyester, a polyurethane, or a polyolefin. A layer having desired physical properties can be formed by appropriately combining these polymers. The total amount of compounds selected from the group consisting of polyamides, polyesters, polyurethanes, and polyolefins contained in the layer other than the innermost layer is equivalent to the total amount contained in the innermost layer.

Each of the polymers that can be used as the polymer cover layer according to the present invention preferably has a molecular weight of 10,000 to 1,000,000, more preferably has a molecular weight of 20,000 to 500,000, and particularly preferably has a molecular weight of 30,000 to 300,000.

In the present invention, the molecular weight of the polymer that forms the polymer cover layer means a weight-average molecular weight unless otherwise noted. The weight-average molecular weight can be measured by gel permeation chromatography (GPC) as a molecular weight in terms of polystyrene.

As illustrated in FIG. 2, the polymer cover layer 15 in the present invention is preferably formed so as to have a substantially uniform thickness in the longitudinal direction (axial direction) of the flexible-tube base 14. The polymer cover layer 15 has a thickness of, for example, 0.2 mm to 1.0 mm. An outer diameter D of the flexible tube 3a is appropriately determined according to the purpose. The outer diameter D is, for example, 11 to 14 mm. In FIG. 2, the inner layer 17 and the outer layer 18 are formed such that the proportions of the thicknesses of the layers 17 and 18 relative to the total thickness of the polymer cover layer 15 change in the axial direction of the flexible-tube base 14. Specifically, the proportion of the thickness of the inner layer 17 relative to the total thickness of the polymer cover layer 15 is larger than that of the outer layer 18 on one end 14a side (distal end side) of the flexible-tube base 14 to be attached to the angle portion 3b. The thickness of the inner layer 17 gradually decreases from the one end 14a toward the other end 14b side (proximal end side) to be attached to the main-body operation section 5. On the other end 14b side, the thickness of the outer layer 18 is larger than the thickness of the inner layer 17.

In FIG. 2, the proportion of the thickness of the inner layer 17 is maximum at the one end 14a, and the proportion of the thickness of the outer layer 18 is maximum at the other end 14b. The proportion of the thickness of the inner layer 17 to the thickness of the outer layer 18 may be, for example, 9:1 at the one end 14a and may be, for example, 1:9 at the other end 14b. The thicknesses of the two layers are changed such that the proportion of the thickness of the inner layer 17 to the thickness of the outer layer 18 is reversed from the end 14a to the end 14b. With this configuration, the flexible tube 3a has a difference in hardness between the one end 14a side and the other end 14b side, and flexibility can be changed in the axial direction such that the one end 14a side is soft and the other end 14b side is hard. The proportion of the thickness of the inner layer to the thickness of the outer layer is preferably 95:5 to 60:40 (inner layer:outer layer) at the one end and is preferably 5:95 to 40:60 (inner layer:outer layer) at the other end.

When the proportion of the thickness of the inner layer 17 to the thickness of the outer layer 18 is within the range of 95:5 to 5:95, the amount of extrusion of a polymer that forms a layer having a smaller thickness can also be accurately controlled.

The soft polymer used in the inner layer 17 and the hard polymer used in the outer layer 18 preferably have a difference in 100% modulus, which is an indicator indicating a hardness after molding, of 1 MPa or more and more preferably 3 MPa or more. The difference in melt viscosity, which is an indicator indicating a fluidity of a polymer in a molten state, at a molding temperature of 150° C. to 300° C. is preferably 2,500 Pa·s or less. With this configuration, the polymer cover layer 15 composed of the inner layer 17 and the outer layer 18 is reliably provided with both good molding accuracy and the required difference in hardness between the distal end side and the proximal end side.

Topcoat Layer

In the flexible tube according to the present invention, the topcoat layer 16 is disposed on the outer periphery of the polymer cover layer 15 as needed. Examples of materials that can be applied to the topcoat layer include, but are not particularly limited to, urethane coatings, acrylic coatings, fluorine coatings, silicone coatings, epoxy coatings, and polyester coatings.

Main purposes of use of the topcoat layer are to protect the surface of the flexible tube or make the surface glossy, to impart slidability, and to impart chemical resistance. Therefore, the topcoat layer preferably has a high modulus of elasticity, a smooth surface, and good chemical resistance.

Method for Producing Flexible Tube
Formation of Porous Layer

In the production of the flexible tube according to the present invention, a porous layer is formed on a flexible-tube base. The porous layer can be formed with reference to, for example, JP2010-77358A, JP2013-18966A, JP2010-64932A, WO2003/028097A, WO2003/075335A, JP2003-115486A, JP2005-202240A, JP2003-268356A, and WO2008/093731A.

The method for producing a flexible tube according to the present invention preferably includes forming a porous layer having an average pore size of 50 nm to 100 μm. As described later, the average pore size of the porous layer can be controlled by, for example, the raw material of the porous layer.

Hereinafter, a method for forming a porous epoxy resin layer and a method for forming a porous silica layer will be specifically described. The following description is merely an example, and the formation of the porous layer in the present invention is not limited to these embodiments.

Method for Forming Porous Silica Layer

A porous silica layer can be formed on (the outer periphery of) a flexible-tube base through the following steps (i) and (ii).

(i) An alkoxysilane compound is subjecting to a dehydration condensation reaction in the presence of a pore-forming agent to prepare a silica composition.

(ii) After the silica composition is applied onto a flexible-tube base, the silica composition is dried (or heated) to form a coating film, and the coating film is further heated at a high temperature to remove the pore-forming agent by decomposition, thereby forming pores in the coating film.

In the step (i), in a liquid mixture containing an alkoxysilane compound, a pore-forming agent, and a solvent, the alkoxysilane compound is subjected to a dehydration condensation reaction to obtain a silica composition.

For example, a silica composition is obtained by mixing an alkoxysilane compound, a pore-forming agent, and a solvent including water, blending a catalyst described later as necessary, subjecting the alkoxysilane compound to a dehydration condensation reaction in the presence of the pore-forming agent while mixing the reaction solution, and concentrating or diluting with a solvent as necessary. The reaction conditions (reaction temperature and reaction time) for the dehydration condensation reaction may be in accordance with ordinary methods.

The alkoxysilane compound is not particularly limited, and tetraalkoxysilane compounds, trialkoxysilane compounds, dialkoxysilane compounds, and the like can be appropriately used.

Examples of the tetraalkoxysilane include, but are not particularly limited to, tetramethoxysilane, tetraethoxysilane, tetrapropoxysilane, tetraisopropoxysilane, and tetrabutoxysilane.

Examples of the trialkoxysilane compounds include methyltrimethoxysilane, methyltriethoxysilane, phenyltrimethoxysilane, and phenyltriethoxysilane.

Examples of the dialkoxysilane compounds include dimethyldimethoxysilane and dimethyldiethoxysilane.

The silica content (the content of the dehydration condensation reaction product) in the silica composition is preferably 0.05% by mass or more, more preferably 0.1% by mass or more, still more preferably 0.5% by mass or more, and even more preferably 1% by mass or more, in total. On the other hand, the content of the silane compounds is preferably 70% by mass or less, more preferably 50% by mass or less, still more preferably 40% by mass or less, and even more preferably 20% by mass or less, in total.

The pore-forming agent that can be used is a substance that is included in silica and that can be decomposed and removed by heating. Examples of the pore-forming agent include surfactants. Nonionic surfactants, anionic surfactants, cationic surfactants, and amphoteric surfactants can be used as the surfactants. A nonionic surfactant is preferred, and a nonionic surfactant having a polymer structure is more preferred. When the surfactant is a polymer, the number average molecular weight thereof is, for example, 300 to 5,000.

The content of the surfactant in the silica composition is preferably 0.1% by mass or more, more preferably 1% by mass or more, still more preferably 1.2% by mass or more, and even more preferably 1.4% by mass or more. On the other hand, the content is preferably 50% by mass or less, more preferably 40% by mass or less, and particularly preferably 30% by mass or less.

The solvent is preferably water or a combination of water and a water-soluble organic solvent. Examples of the water-soluble organic solvent include alcohol compounds such as monohydric alcohols having 1 to 5 carbon atoms, e.g., methanol, ethanol, 1-propanol, 2-propanol, 2-methyl-1-propanol, 1-butanol, 2-butanol, t-butanol, and 1-pentanol, dihydric alcohols having 1 to 4 carbon atoms, and polyhydric alcohols, e.g., glycerin and pentaerythritol; etherified products and esterified products of the above alcohol compounds, such as methyl acetate, ethyl acetate, isobutyl acetate, diethylene glycol, ethylene glycol monomethyl ether, ethylene glycol dimethyl ether, 2-ethoxyethanol, propylene glycol monomethyl ether, and propylene glycol methyl ether acetate; ketone compounds such as acetone and methyl ethyl ketone; amide compounds such as formamide, N-methylformamide, N-ethylformamide, N,N-dimethylformamide, N,N-diethylformamide, N-methylacetamide, N-ethylacetamide, N,N-dimethylacetamide, N,N-diethylacetamide, N-methylpyrrolidone, N-formylmorpholine, N-acetylmorpholine, N-formylpiperidine, N-acetylpiperidine, N-formylpyrrolidine, N-acetylpyrrolidine, N,N'-diformylpiperazine, and N,N'-diacetylpiperazine; lactone compounds such as γ-butyrolactone; ureas such as tetramethylurea and N,N'-dimethylimidazolidine; and dimethyl sulfoxide. Of these, alcohols are preferred, and monohydric alcohols are more preferred in order to hydrolyze the contained alkoxysilane compound under more stable conditions.

The silica composition usually contains a catalyst. Any substance that promotes the hydrolysis and dehydration condensation reaction of the alkoxysilane compound may be used as the catalyst.

Examples thereof include acids such as hydrofluoric acid, phosphoric acid, boric acid, hydrochloric acid, nitric acid, sulfuric acid, formic acid, acetic acid, oxalic acid, maleic acid, methylmalonic acid, stearic acid, linoleic acid, benzoic acid, phthalic acid, citric acid, and succinic acid; amine compounds such as ammonia, butylamine, dibutylamine, and triethylamine; bases such as pyridine; and Lewis acids such as an acetylacetone complex of aluminum.

Examples of the catalyst further include metal chelate compounds. Examples of the metal species in the metal chelate compounds include titanium, aluminum, zirconium, tin, and antimony.

The silica composition may contain components other than the alkoxysilane compound, the organic solvent, the surfactant, water, and the catalyst as long as the effects of the present invention are not impaired.

In the step (ii), a flexible-tube base is immersed in the silica composition obtained in the step (i), and the flexible-tube base is then taken out and dried to form a coating film. Subsequently, the surfactant is removed by decomposition at a high temperature (for example, 250° C. or higher). Thus, a flexible-tube base having a porous silica layer can be obtained.

The average pore size and the porosity of the porous silica layer can be controlled by, for example, the types of raw materials, the blending ratio of the raw materials, and reaction conditions (for example, drying or heating temperature, and heating time).

Method for Forming Porous Epoxy Resin Layer

A porous epoxy resin layer can be formed on (the outer periphery of) a flexible-tube base through the following steps (1) to (3).

(1) A liquid mixture containing an epoxy resin, a pore-forming agent, a solvent, and a curing agent for the epoxy resin is prepared.

(2) The liquid mixture is applied onto a flexible-tube base, dried, and then heated to cause the epoxy resin to reach with the curing agent.

(3) The pore-forming agent is removed from the cured epoxy resin.

In the step (1), a liquid mixture containing an epoxy resin, a curing agent, and a pore-forming agent is prepared. This mixing is performed at room temperature (for example, 25° C. to 30° C.) or a lower temperature for about 5 to 30 minutes to obtain a homogeneous mixture.

As the epoxy resin, aromatic epoxy resins and non-aromatic epoxy resins may be used.

Examples of aromatic epoxy resins include polyphenyl-based epoxy resins, fluorene ring-containing epoxy resins, triglycidyl isocyanurate-containing epoxy resins, and heteroaromatic ring (e.g., triazine ring)-containing epoxy resins.

Examples of polyphenyl-based epoxy resins include bis-phenol A-type epoxy resins, brominated bisphenol A-type epoxy resins, bisphenol F-type epoxy resins, bisphenol AD-type epoxy resins, stilbene-type epoxy resins, biphenyl-type epoxy resins, bisphenol A-novolac-type epoxy resins, cresol-novolac-type epoxy resins, diaminodiphenylmeth-ane-type epoxy resins, and tetrakis(hydroxyphenyl)ethane-based epoxy resins.

Examples of non-aromatic epoxy resins include aliphatic glycidyl ether-type epoxy resins, aliphatic glycidyl ester-type epoxy resins, alicyclic glycidyl ether-type epoxy resins, alicyclic glycidyl amine-type epoxy resins, and alicyclic glycidyl ester-type epoxy resins.

The above epoxy resins may be used alone or in combination of two or more thereof.

As the curing agent, typical curing agents such as amine compounds, acid anhydrides, and imidazole compounds used for curing epoxy resins may be used. Examples of amine compounds include 1,6-diaminohexane, 1,4-diaminobutane, and 1,8-diaminooctane. The above curing agents may be used alone or in combination of two or more thereof.

The ratio of the content of the curing agent relative to the epoxy resin in the liquid mixture in the step (1) is, for example, preferably 0.1 to 1.5, and more preferably 0.2 to 1.0, in terms of curing agent equivalent, relative to 1 equivalent of the epoxy group in the epoxy resin.

Specific examples of the pore-forming agent include cellosolve compounds such as methyl cellosolve and ethyl cellosolve, ester compounds such as ethylene glycol monomethyl ether acetate and propylene glycol monomethyl ether acetate, glycol compounds such as polyethylene glycol and polypropylene glycol, and ether compounds such as polyoxyethylene monomethyl ether and polyoxyethylene dimethyl ether. The above pore-forming agents may be used alone or in combination of two or more thereof.

The ratio of the content of the pore-forming agent to the total content of the epoxy resin, the curing agent, and the pore-forming agent may be, for example, 10% to 80% by mass.

The solvent is a solvent capable of dissolving components such as the epoxy resin, the curing agent, and the pore-forming agent. For example, organic solvents such as methyl ethyl ketone, acetone, toluene, cyclohexanone, and methyl isobutyl ketone (MIBK) are preferred.

In the step (2), the liquid mixture is applied to the surface of a flexible-tube base by, for example, immersing the flexible-tube base in the liquid mixture prepared in the step (1). Subsequently, drying is performed to remove the solvent, and heating is performed, for example, at about 60° C. to 120° C. for 30 minutes to 4 hours. Thus, an epoxy resin layer can be formed on the flexible-tube base.

In the step (3), the pore-forming agent is removed from the epoxy resin layer by, for example, immersing the flexible-tube base in a solvent that does not dissolve the epoxy resin but dissolves the pore-forming agent, while ultrasonic treatment is performed as required. Examples of the solvent that does not dissolve the epoxy resin but dissolves the pore-forming agent include water and a liquid mixture of water and at least one of N,N-dimethylformamide (DMF), dimethyl sulfoxide (DMSO), or tetrahydrofuran (THF).

The average pore size and the porosity of the porous epoxy resin layer can be controlled by, for example, the types of raw materials, the blending ratio of the raw materials, and reaction conditions (for example, heating temperature and heating time in reaction-induced phase separation).

In the present invention, a portion that is not covered with the porous layer may be present on the outer periphery of the flexible-tube base (that is, a portion of the porous layer may have a void) as long as the effects of the present invention are not impaired.

Prior to the formation of the porous layer, the flexible-tube base is preferably cleaned by degreasing with an acid solution, an alkali solution, an aqueous solution of a surfactant, an organic solvent, or the like. After the cleaning, the flexible-tube base is preferably further cleaned with water or hot water so that the amount of an acid, an alkali, a surfactant, or the like decreases from the surface of the base.

Formation of Primer Layer

In the production of the flexible-tube base according to the present invention, after the porous layer is formed, a primer layer is formed on the porous layer. The primer layer can be formed by dissolving at least one of a silane coupling agent, a titanium coupling agent, a zirconium coupling agent, or an aluminum coupling agent in a solvent to prepare a coating liquid; forming a coating film on at least the outer periphery of the flexible-tube base by, for example, applying or spraying the coating liquid onto the outer periphery of the flexible-tube base or immersing the flexible-tube base into the coating liquid; and subsequently drying the coating film by an ordinary method (for example, drying at a high temperature of about 100° C.).

Examples of the solvent that can be used in the coating liquid include alcohol solvents such as methanol and ethanol; ketone solvents such as acetone and methyl ethyl ketone; ester solvents such as ethyl acetate; hydrocarbon solvents such as toluene; and liquid mixtures thereof. It is preferable to further mix water or an acid catalyst such as acetic acid with the solvents in order to accelerate hydrolysis of the silane coupling agent, the titanium coupling agent, the zirconium coupling agent, and the aluminum coupling agent. The coating liquid may be prepared to be acidic (for example, pH 1 to 4 at 25° C.) or alkaline (for example, pH 9 to 11 at 25° C.).

The content of the silane coupling agent, the titanium coupling agent, the zirconium coupling agent, and the aluminum coupling agent in the coating liquid is not particularly limited. For example, the content may be 0.01% to 2% by mass and is preferably 0.05% by mass or more and less than 1.5% by mass, and more preferably 0.1% by mass or more and less than 1.0% by mass, in total.

The coating liquid may include, for example, a surfactant and a catalyst in addition to at least one of a silane coupling agent, a titanium coupling agent, a zirconium coupling agent, or an aluminum coupling agent, a solvent, and a pH adjuster. The coating liquid is more preferably composed of at least one of a silane coupling agent, a titanium coupling agent, a zirconium coupling agent, or an aluminum coupling agent, and a solvent.

In the present invention, a portion that is not covered with the primer layer may be present on the porous layer (that is, a portion of the primer layer may have a void) as long as the effects of the present invention are not impaired.

Formation of Polymer Cover Layer

Formation of a polymer cover layer will be described by taking, as an example, a case where the polymer cover layer has a two-layer structure.

A flexible tube that includes a polymer cover layer having a two-layer structure composed of an inner layer and an outer layer can be produced by, for example, melt-kneading and extruding, around the flexible-tube base on which the primer layer has been formed, a first polymer material (a polymer material including at least one compound of a polyamide, a polyester, a polyurethane, or a polyolefin) that constitutes the inner layer and a second polymer material that constitutes the outer layer to cover the flexible-tube base.

In an embodiment in which the polymer cover layer is formed of one layer or three or more layers, the polymer cover layer can also be obtained by appropriately changing the layer configuration with reference to the method described below.

Figure 3:
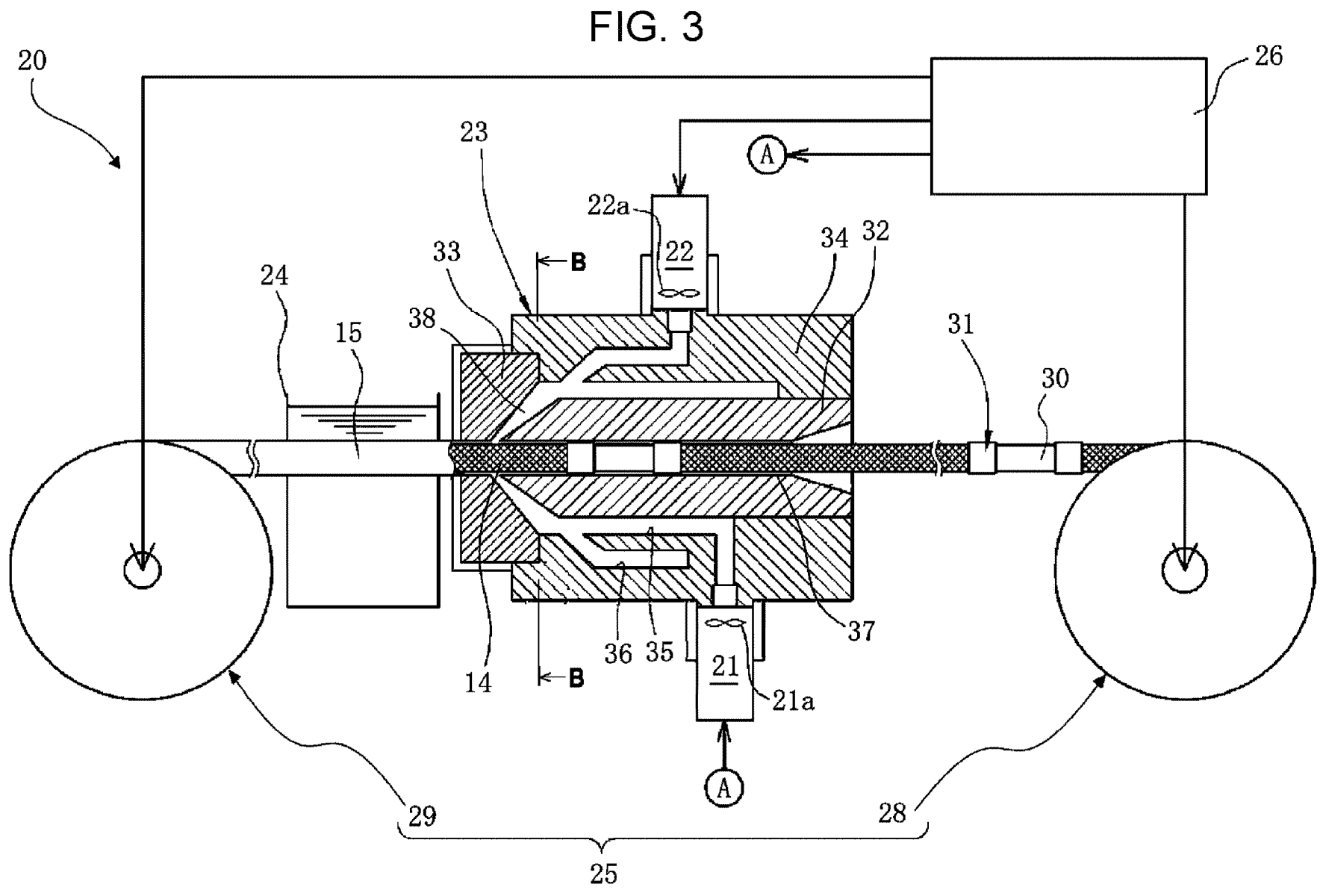
Figure 4:
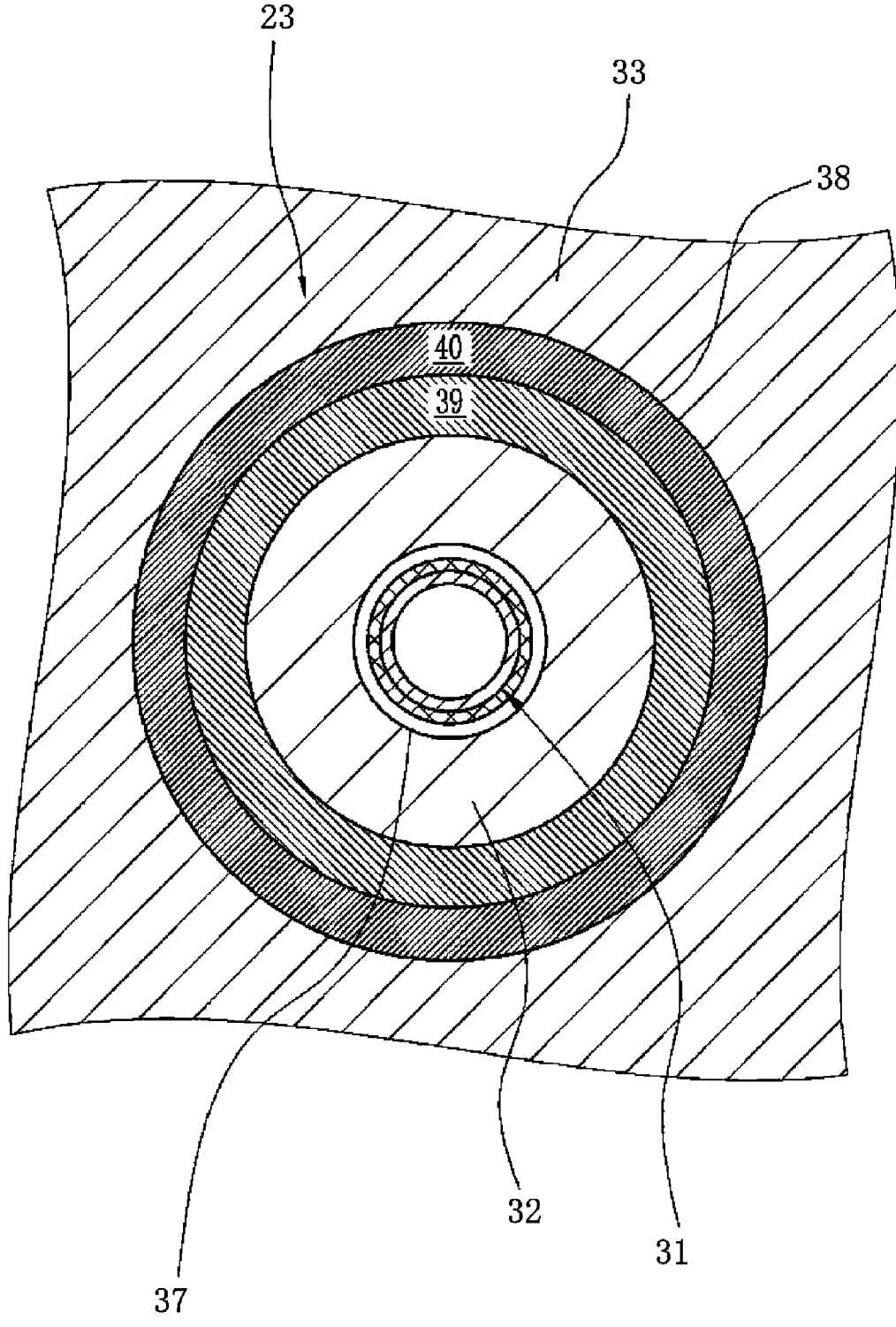
FIG. 4 is a sectional view taken along line B-B in FIG. 3.

An example of a method for forming a polymer cover layer of the flexible tube 3a (FIGS. 1 and 2) will be described with reference to FIGS. 3 and 4. In this embodiment, a continuous molding machine is used to mold a polymer cover layer 15. It is preferable to use a continuous molding machine 20 that includes well-known extrusion units 21 and 22 including hoppers, screws 21a and 22a, etc.; a head unit 23 configured to mold a polymer cover layer 15 so as to cover an outer peripheral surface of a flexible-tube base 14; a cooling unit 24; a transport unit 25 (including a feed drum 28 and a take-up drum 29) configured to transport a connected flexible-tube base 31 to the head unit 23; and a control unit 26 configured to control the above units. The head unit 23 preferably includes a nipple 32, a die 33, and a support 34 configured to fixedly support the nipple 32 and the die 33. For example, the apparatus disclosed in FIGS. 3 to 5 of JP2011-72391A can be used as an example of the apparatus having the above configuration.

The inside of the die 33 is preferably heated to a predetermined molding temperature. The molding temperature is preferably set in a range of 150° C. to 300° C. The temperatures of a first polymer material 39 and a second polymer material 40 can be increased by controlling the temperatures of a heating unit in the apparatus by heating. In addition to this, as the rotational speeds of the screws 21a and 22a become higher, the temperatures of the first polymer material 39 and the second polymer material 40 can be further increased to increase their fluidity. During this process, the molding thicknesses of the inner layer 17 and the outer layer 18 can be adjusted by changing the amounts of the molten first polymer material 39 and second polymer material 40 ejected while the transport speed of the connected flexible-tube base 31 is made constant.

The process of molding the polymer cover layer 15 on the connected flexible-tube base 31 by the continuous molding machine 20 will be described. When the continuous molding machine 20 performs a molding step, the molten first polymer material 39 and second polymer material 40 are respectively extruded from the extrusion units 21 and 22 into the head unit 23. At the same time, the transport unit 25 operates so that the connected flexible-tube base 31 is transported to the head unit 23. During this process, the extrusion units 21 and 22 are in a state of constantly extruding the first polymer material 39 and the second polymer material 40 to feed the polymer materials 39 and 40 to the head unit 23, and the first polymer material 39 and the second polymer material 40 that are respectively extruded from the extrusion units 21 and 22 to gates 35 and 36 pass through an edge and join to each other, and are fed, in a stacked state, through a polymer passage 38 to a molding passage 37. As a result, a two-layer molded polymer cover layer 15 is formed in which an inner layer 17 using the first polymer material 39 and an outer layer 18 using the second polymer material 40 are stacked.

The connected flexible-tube base 31 includes a plurality of flexible-tube bases 14 (having a porous layer and a primer layer on the outer peripheries of the flexible-tube bases 14) that are connected together. While the connected flexible-tube base 31 is transported through the molding passage 37, the polymer cover layer 15 is continuously molded on the plurality of flexible-tube bases 14. When the polymer cover layer 15 is molded from one end 14a side (distal end side) of one flexible-tube base to the other end 14b side (proximal end side) thereof, the thickness of the inner layer 17 is made large immediately after the extrusion units 21 and 22 start the ejection of the polymers. The proportion of the thickness of the outer layer 18 is then gradually increased over an intermediate portion toward the other end 14b side. It is preferable to control the amounts of the polymers ejected in this manner such that the polymer cover layer 15 has the gradient thickness proportion described above.

Joint members 30 each function as a connecting portion of two flexible-tube bases 14, and thus the control unit 26 is used to switch the amounts of the polymers ejected from the extrusion units 21 and 22. Specifically, the control unit 26 preferably switches the amounts of the polymers ejected from the extrusion units 21 and 22 such that the thickness proportion changes from a thickness proportion on the other end 14b side (proximal end side) of one flexible-tube base 14 to a thickness proportion on one end 14a side (distal end side) of the next flexible-tube base 14. When the polymer cover layer 15 is molded from the one end 14a side of the next flexible-tube base 14 to the other end 14b side thereof, the extrusion units 21 and 22 are preferably similarly controlled such that the thickness of the outer layer gradually increases from the one end side toward the other end side.

The connected flexible-tube base 31 on which the polymer cover layer 15 is molded to the rearmost end is removed from the continuous molding machine 20, and the joint members 30 are then removed from the flexible-tube bases 14 to separate the flexible-tube bases 14 from each other. Next, for each of the separated flexible-tube bases 14, the polymer cover layer 15 is coated with the topcoat layer 16 to complete flexible tubes 3a. The completed flexible tubes 3a are transported to an assembly step of an electronic endoscope.

In the present invention, when the polymer cover layer is formed of a plurality of layers, a functional layer may be disposed between layers constituting the plurality of layers.

The above description has been made with reference to the drawings by taking, as an example, an electronic endoscope configured to observe an image of the condition of a subject picked up with an imaging device; however, the present invention is not limited to this and is also applicable to an endoscope configured to observe the condition of a subject by using an optical image guide.

The flexible tube according to the present invention is widely applicable to endoscopic medical devices. For example, the flexible tube according to the present invention is applicable to an endoscope equipped with a clip or wire at the distal end thereof or to a device equipped with a basket or brush. Note that the term "endoscopic medical device" is meant to broadly include medical devices or diagnosis and treatment devices that include an insertion section having flexibility and that are introduced and used in the body, such as remote-controlled medical devices, in addition to medical devices including an endoscope as a basic structure, as described above.

An endoscopic medical device according to the present invention has an insertion section in which the flexible tube for an endoscope according to the present invention is incorporated. That is, a method for producing an endoscopic medical device according to the present invention includes incorporating the flexible tube for an endoscope according to the present invention into an insertion section of an endoscopic medical device.

EXAMPLES

Hereinafter, the present invention will be described in more detail by way of Examples; however, these Examples should not be construed as limiting the present invention.
Production of Flexible Tube for Endoscope Flexible tubes having the structure illustrated in FIG. 2 were produced. The polymer cover layer had a single-layer structure or a two-layer structure as shown in Table 3 below.
Flexible-Tube Base Flexible-tube bases were each prepared by forming a spiral tube 11 using a metal strip 11a made of stainless steel (SUS304), and covering the spiral tube 11 with a tubular mesh member 12 obtained by weaving fibers made of SUS304. The flexible-tube bases have a length of 80 cm and a diameter of 12 mm. The stainless steel flexible tube bases each have a passivation layer on a surface thereof, the passivation layer being formed by annealing treatment (heating treatment) during the formation of the spiral tube and the tubular mesh member.

The flexible-tube bases were cleaned by degreasing with acetone and then immersing in a 1 N aqueous sodium hydroxide solution at 50° C. for three minutes. Subsequently, rinsing was performed with distilled water three times, and drying was then performed in an oven heated to 100° C. for 10 minutes to prepare flexible-tube bases.
Formation of Porous Epoxy Resin Layer (L-1)

In a stainless steel vessel, 10.0 g of a bisphenol A-type epoxy resin ("jER828" (trade name), manufactured by Mitsubishi Chemical Corporation, epoxy equivalent: 184 to 194 g/eq.), 4.0 g of polyethylene glycol ("SANNIX PEG-400" (trade name), manufactured by Sanyo Chemical Industries, Ltd.), and 1950.0 g of methyl ethyl ketone were mixed to prepare a methyl ethyl ketone solution of epoxy resin/polyethylene glycol. After 15.0 g of 1,6-diaminohexane was added to this solution, the solution was stirred at room temperature for 15 minutes using a three-one motor to prepare an epoxy resin solution (D).

The flexible-tube base after cleaning was immersed in the epoxy resin solution (D) for five minutes, then pulled up, and air-dried at 40° C. for 30 minutes to volatilize the methyl ethyl ketone. The flexible-tube base was heated in an oven at 100° C. for three hours to form an epoxy resin layer on the outer periphery of the flexible-tube base.

Next, the flexible-tube base having the epoxy resin layer thereon was subjected to ultrasonic cleaning for 10 minutes in a liquid mixture of distilled water/dimethylformamide=1/1 (v/v), then subjected to ultrasonic cleaning for 10 minutes with distilled water alone, and further immersed in distilled water for 12 hours to remove the polyethylene glycol included therein.

Subsequently, drying at 80° C. was conducted for two hours to form a porous epoxy resin layer (L-1) on the outer periphery of the flexible-tube base.
Formation of Porous Epoxy Resin Layers (L-2) to (L-9)

Porous epoxy resin layers (L-2) to (L-9) were formed on the outer peripheries of the flexible-tube bases as in the porous epoxy resin layer (L-1) except that the components shown in Table 1 below were used. Specifically, flexible-tube bases having the porous epoxy resin layers (L-2) to (L-9) on the outer peripheries thereof were obtained.
Formation of Porous Silica Layer (L-10)

In a stainless steel vessel, 1,000 g of a hydrolyzed silicate ("HAS-1" (trade name), manufactured by Nippon Colcoat Co., Ltd., solid content: 21% by mass, 2-propanol/ethanol/methanol solvent), 45 g of polyethylene glycol ("SANNIX PEG-400" (trade name), manufactured by Sanyo Chemical Industries, Ltd.), and 955 g of isopropyl alcohol were mixed to prepare a silica composition (a).

The flexible-tube base after cleaning was immersed in the silica composition (a) for five minutes, then pulled up, and air-dried at 40° C. for 30 minutes to volatilize the solvent. The flexible-tube base was heated in an oven at 100° C. for 10 minutes to form a silica layer on the outer periphery of the flexible-tube base.

Next, the flexible-tube base having the silica layer thereon was subjected to ultrasonic cleaning for 10 minutes in a liquid mixture of distilled water/dimethylformamide=1/1 (v/v), then subjected to ultrasonic cleaning for 10 minutes with distilled water alone, and further immersed in distilled water for 12 hours to remove the polyethylene glycol included therein.

Subsequently, drying was conducted at 80° C. for two hours to form a porous silica layer (L-10) on the outer periphery of the flexible-tube base.
Formation of Porous Silica Layers (L-11) to (L-13)

Porous silica layers (L-11) to (L-13) were formed on the outer peripheries of the flexible-tube bases as in the porous silica layer (L-10) except that the components shown in Table 2 below were used. Specifically, flexible-tube bases having the porous silica layers (L-11) to (L-13) on the outer peripheries thereof were obtained.
Formation of Non-porous Epoxy Layer (R-1)

An epoxy resin layer (R-1) having no pores was formed in the same manner except that the polyethylene glycol was not used in the formation of the porous epoxy layer (L-1).

23

Formation of Non-porous Silica Layer (R-2)

A silica layer (R-2) having no pores was formed in the same manner except that polyethylene glycol was not used in the formation of the porous silica layer (L-10).

The average pore size, the porosity, and the average layer thickness of each porous layer were measured and calculated as described below. The measurement results are shown in Tables 1 and 2 below.

Average Pore Size and Porosity

A flexible tube placed in an oven set at 150° C. for four hours and then allowed to stand in a desiccator until the temperature reached room temperature was used for the measurement.

The measurement was conducted by mercury intrusion porosimetry with a porosimeter ("PoreSizer 9320" (trade name), manufactured by Micromeritics Instrument Corporation). In the measurement, the initial pressure was 20 kPa, the measured pore size was 3 nm to 400 μm, the measurement mode was a pressure-rising (intrusion) process, the measuring cell volume was about 6 cm$^3$, the mercury contact angle was 130°, and the mercury surface tension was 484 dyn/cm.

Average Layer Thickness

The flexible-tube base produced as described above was cut at five positions at random, and each cross section of the porous layer was observed with a scanning electron microscope (S-5500 (trade name), manufactured by Hitachi High-Tech Corporation) at a magnification of 50,000. Thus, the thickness of the porous layer formed on the outer periphery was determined at one point in each cross section. The number-average value was calculated from the five determined values.

24

Notes in Tables 1 and 2

The amount used is expressed in units of "g".

jER828: Bisphenol A-type epoxy resin ("jER828" (trade name), manufactured by Mitsubishi Chemical Corporation, epoxy equivalent: 184 to 194 g/eq.)

HAS-1: Trade name, manufactured by Nippon Colcoat Co., Ltd., solid content: 21% by mass, 2-propanol/ethanol/methanol solvent PEG: Polyethylene glycol ("SANNIX PEG-400" (trade name), manufactured by Sanyo Chemical Industries, Ltd.)

PP-400: Polypropylene glycol ("SANNIX PP-400" (trade name), manufactured by Sanyo Chemical Industries, Ltd.)

PP-1000: Polypropylene glycol ("SANNIX PP-1000" (trade name), manufactured by Sanyo Chemical Industries, Ltd.)

PP-3000: Polypropylene glycol ("SANNIX PP-3000" (trade name), manufactured by Sanyo Chemical Industries, Ltd.)

DAH: 1,6-Diaminohexane

MEK: Methyl ethyl ketone

IPA: Isopropyl alcohol

Formation of Primer Layer

A coating liquid for forming a primer layer was prepared by mixing 150 g of ethanol, 350 g of water, and 1.0 g of N-2-(aminoethyl)-3-aminopropylmethyldimethoxysilane (S-1, trade name: KBM-603, manufactured by Shin-Etsu Chemical Co., Ltd.).

The flexible-tube base having the porous layer was immersed in the above-prepared coating liquid for forming a primer layer at room temperature for one minute, air-dried for 10 minutes, then placed in an oven at 100° C., and dried

TABLE 1

| | Porous epoxy resin layer | | | | | | | | |
| | (L-1) | (L-2) | (L-3) | (L-4) | (L-5) | (L-6) | (L-7) | (L-8) | (L-9) |
|---|---|---|---|---|---|---|---|---|---|
| jER828 | 10.0 | 10.0 | 10.0 | 10.0 | 10.0 | 10.0 | 10.0 | 10.0 | 10.0 |
| PEG | 4.0 | 6.5 | 10.0 | | | | | | |
| PP-400 | | | | 14.7 | 18.0 | | | | |
| PP-1000 | | | | | | 20.0 | 27.0 | | |
| PP-3000 | | | | | | | | 30.0 | 35.0 |
| DAH | 15.0 | 15.0 | 15.0 | 15.0 | 15.0 | 15.0 | 15.0 | 15.0 | 15.0 |
| MEK | 1,950.0 | 1,950.0 | 1,950.0 | 1,950.0 | 1,950.0 | 1,950.0 | 1,950.0 | 1,950.0 | 1,950.0 |
| Average pore size | 80 nm | 200 nm | 560 nm | 1.2 μm | 4.5 μm | 11μm | 85 μm | 140 μm | 250 μm |
| Porosity (%) | 17 | 25 | 31 | 35 | 41 | 45 | 53 | 55 | 58 |
| Average layer thickness (μm) | 0.24 | 0.61 | 1.8 | 3.8 | 16 | 42 | 320 2 | 530 | 860 |

TABLE 2

| | Porous silica layer | | | |
| | (L-10) | (L-11) | (L-12) | (L-13) |
|---|---|---|---|---|
| HAS-1 | 1,000 | 1,000 | 1,000 | 1,000 |
| PEG | 45 | | | |
| PP-400 | | 60 | | |
| PP-1000 | | | 80 | |
| PP-3000 | | | | 120 |
| IPA | 955 | 940 | 920 | 880 |
| Average pore size | 90 nm | 220 nm | 540 nm | 1.1 um |
| Porosity (%) | 18 | 23 | 29 | 36 |
| Average layer thickness (μm) | 0.31 | 0.65 | 2.0 | 4.1 | by heating for 10 minutes to prepare a flexible-tube base having a primer layer on the porous layer (flexible-tube base used in Example 1).

In the same manner as described above, flexible-tube bases used in Examples and Comparative Examples were prepared using the coupling agents as shown in Table 3. In Comparative Examples, an interlayer was formed instead of the porous layer of Examples. In Comparative Example 4, no primer layer was formed.

Formation of Polymer Cover Layer

The outer peripheries of the flexible-tube bases having the primer layer on the porous layer were each covered with a polymer as shown in Table 3 (Tables 3-1 and 3-2) below by extrusion (molding temperature: melting point of polymer+ 10° C.) to produce flexible tubes for endoscopes, the flexible tubes having a polymer cover layer. The polymer cover layer had a thickness of 0.4 mm (in the cases of a two-layer structure, the total thickness of the two layers was 0.4 mm).

In the cases where the polymer cover layer was formed of two layers (Examples 1 to 36 and 44 to 51 and Comparative Examples 1 to 4 and 6 to 8), the outer periphery was simultaneously covered with the two layers by two-layer extrusion molding. In these cases, the proportion of the inner layer to the outer layer at the distal end and the proportion at the proximal end were inner layer:outer layer=80:20 at the distal end and inner layer:outer layer=20:80 at the proximal end, respectively. The thicknesses of the inner layer and the outer layer were changed in a gradient manner from the distal end toward the proximal end.

Each of the produced flexible tubes was subjected to the following tests. The results are summarized in Table 3 below.

[Test Example 1] Evaluation of Elasticity of Flexible Tube

In an environment at a temperature of 25° C. and a relative humidity of 50%, positions 30 cm and 50 cm from one tip portion of the above-produced flexible tube for an endoscope were fixed, and a position of 40 cm (central portion of the flexible tube) was pushed by 15 mm in a direction (diameter direction) perpendicular to the length direction of the flexible tube. A ratio of a repulsive force (b) after 30 seconds to a repulsive force (a) after 0.1 seconds was calculated as an elasticity (%). The repulsive force was measured with a force gauge (ZTS50N (trade name), manufactured by IMADA Co., Ltd.).

$$[\text{Elasticity } (\%)]=[(b)/(a)]\times 100$$

The elasticity was evaluated on the basis of the following evaluation criteria. "C" or higher is satisfactory.
Evaluation Criteria for Elasticity
A: The elasticity is 80% or more.
B: The elasticity is 75% or more and less than 80%.
C: The elasticity is 65% or more and less than 75%.
D: The elasticity is less than 65%.

[Test Example 2] Evaluation of Bending Durability (Adhesiveness) of Flexible Tube The above-produced flexible tube for an endoscope was brought into contact, in a U shape, with a semicircular portion of a pulley with a diameter of 7 cm, the flexible tube was reciprocated such that the tip portion and the rear end portion were positioned at 3.5 cm in front of the end of the pulley, and the state of the polymer cover layer was visually observed. The number of reciprocations at which lifting, tearing, or separation of the polymer cover layer occurred was evaluated on the basis of the following evaluation criteria. "C" or higher is satisfactory.
Evaluation Criteria for Bending Durability
A: 10,000 times or more
B: 1,000 times or more and less than 10,000 times
C: 100 times or more and less than 1,000 times
D: less than 100 times

[Test Example 3] Evaluation of Heat Cycle Resistance of Flexible Tube

The above-produced flexible tube for an endoscope was subjected to 500 cycles of a heat cycle test using a thermo-hygrostat (KHWV-40HP (trade name), manufactured by SATAKE MultiMix Corporation), in which each cycle included two hours at 0° C. and two hours at 60° C. For the flexible tube for an endoscope after 500 cycles of the heat cycle test, a repulsive force (c) was measured 0.1 seconds after the flexible tube was pushed in the same manner as in Test Example 1. The ratio of the repulsive force (c) to a repulsive force (a) measured before the heat cycle test in the same manner as in Test Example 1 was calculated as a repulsive force retention ratio (%).

$$[\text{Repulsive force retention ratio } (\%)]=[(c)/(a)]\times 100$$

The repulsive force retention ratio was evaluated on the basis of the following evaluation criteria. "C" or higher is satisfactory.
Evaluation Criteria for Heat Cycle Resistance
A: The repulsive force retention ratio is 90% or more.
B: The repulsive force retention ratio is 70% or more and less than 90%.
C: The repulsive force retention ratio is 50% or more and less than 70%.
D: The repulsive force retention ratio is less than 50%.

TABLE 3-1

| | | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|---|
| Porous layer | Type | (L-1) | (L-2) | (L-3) | (L-4) | (L-5) | (L-6) | (L-7) | (L-8) | (L-9) | (L-10) |
| | Average pore size | 80 nm | 200 nm | 560 nm | 1.2 μm | 4.5 μm | 11 μm | 85 μm | 140 μm | 250 μm | 90 nm |
| | Primer layer | (S-1) | (S-1) | (S-1) | (S-1) | (S-1) | (S-1) | (S-1) | (S-1) | (S-1) | (S-1) |
| Polymer cover layer | Inner layer | (U-1) | (U-1) | (U-1) | (U-1) | (U-1) | (U-1) | (U-1) | (U-1) | (U-1) | (U-1) |
| | Outer layer | (E-1) | (E-1) | (E-1) | (E-1) | (E-1) | (E-1) | (E-1) | (E-1) | (E-1) | (E-1) |
| | Elasticity | A | A | A | A | A | A | A | A | A | A |
| | Bending durability | A | A | AA | AA | A | A | B | C | C | A |
| | Heat cycle resistance | C | B | A | AA | AA | A | A | A | A | C |

| | | Ex. 11 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|---|
| Porous layer | Type | (L-11) | (L-12) | (L-13) | (L-4) | (L-4) | (L-4) | (L-4) | (L-4) | (L-4) | (L-4) |
| | Average pore size | 220 nm | 540 nm | 1.1 μm | 1.2 μm | 1.2 μm | 1.2 μm | 1.2 μm | 1.2 μm | 1.2 μm | 1.2 μm |
| | Primer layer | (S-1) | (S-1) | (S-1) | (S-2) | (S-3) | (S-4) | (S-5) | (S-6) | (S-7) | (S-8) |
| Polymer cover | Inner layer | (U-1) | (U-1) | (U-1) | (U-1) | (U-1) | (U-1) | (U-1) | (U-1) | (U-1) | (U-1) |
| layer | Outer layer | (E-1) | (E-1) | (E-1) | (E-1) | (E-1) | (E-1) | (E-1) | (E-1) | (E-1) | (E-1) |

TABLE 3-1-continued

| | | | | | | | | | | |
|---|---|---|---|---|---|---|---|---|---|---|
| Elasticity | A | A | A | A | A | A | A | A | A | A |
| Bending durability | A | AA | AA | AA | A | AA | AA | B | A | A |
| Heat cycle resistance | B | A | AA | AA | AA | A | A | A | B | B |

| | | Ex. 21 | Ex. 22 | Ex. 23 | Ex. 24 | Ex. 25 | Ex. 26 | Ex. 27 | Ex. 28 | Ex. 29 | Ex. 30 |
|---|---|---|---|---|---|---|---|---|---|---|---|
| Porous layer | Type | (L-4) | (L-4) | (L-4) | (L-4) | (L-4) | (L-4) | (L-4) | (L-4) | (L-4) | (L-4) |
| | Average pore size | 1.2 μm | 1.2 μm | 1.2 μm | 1.2 μm | 1.2 μm | 1.2 μm | 1.2 μm | 1.2 μm | 1.2 μm | 1.2 μm |
| Primer layer | | (S-9) | (A-1) | (A-2) | (A-3) | (A-4) | (A-5) | (Z-1) | (Z-2) | (Z-3) | (Z-4) |
| Polymer cover layer | Inner layer | (U-1) | (U-1) | (U-1) | (U-1) | (U-1) | (U-1) | (U-1) | (U-1) | (U-1) | (U-1) |
| | Outer layer | (E-1) | (E-1) | (E-1) | (E-1) | (E-1) | (E-1) | (E-1) | (E-1) | (E-1) | (E-1) |
| Elasticity | | A | B | B | A | A | B | B | C | B | B |
| Bending durability | | A | C | B | B | B | B | C | C | B | C |
| Heat cycle resistance | | B | C | B | B | B | C | B | B | B | B |

| | | Ex. 31 | Ex. 32 | Ex. 33 | Ex. 34 | Ex. 35 | Ex. 36 | Ex. 37 | Ex. 38 | Ex. 39 | Ex. 40 |
|---|---|---|---|---|---|---|---|---|---|---|---|
| Porous layer | Type | (L-4) | (L-4) | (L-4) | (L-4) | (L-4) | (L-4) | (L-4) | (L-4) | (L-4) | (L-4) |
| | Average pore size | 1.2 μm | 1.2 μm | 1.2 μm | 1.2 μm | 1.2 μm | 1.2 μm | 1.2 μm | 1.2 μm | 1.2 μm | 1.2 μm |
| Primer layer | | (Z-5) | (T-1) | (T-2) | (T-3) | (T-4) | (T-5) | (S-1) | (S-1) | (S-1) | (S-1) |
| Polymer cover layer | Inner layer | (U-1) | (U-1) | (U-1) | (U-1) | (U-1) | (U-1) | (U-1) | (U-2) | (U-3) | (U-4) |
| | Outer layer | (E-1) | (E-1) | (E-1) | (E-1) | (E-1) | (E-1) | Single layer | Single layer | Single layer | Single layer |
| Elasticity | | C | B | B | A | A | A | C | C | C | C |
| Bending durability | | C | B | B | B | A | B | A | A | A | A |
| Heat cycle resistance | | C | C | C | A | B | A | A | A | A | A |

| | | Ex. 41 | Ex. 42 | Ex. 43 | Ex. 44 | Ex. 45 | Ex. 46 | Ex. 47 | Ex. 48 | Ex. 49 | Ex. 50 |
|---|---|---|---|---|---|---|---|---|---|---|---|
| Porous layer | Type | (L-4) | (L-4) | (L-4) | (L-4) | (L-4) | (L-4) | (L-4) | (L-4) | (L-4) | (L-4) |
| | Average pore size | 1.2 μm | 1.2 μm | 1.2 μm | 1.2 μm | 1.2 μm | 1.2 μm | 1.2 μm | 1.2 μm | 1.2 μm | 1.2 μm |
| Primer layer | | (S-1) | (S-1) | (S-1) | (S-1) | (S-1) | (S-1) | (S-1) | (S-1) | (S-1) | (S-1) |
| Polymer cover layer | Inner layer | (E-1) | (Ae-1) | (P-1) | (E-1) | (U-2) | (U-3) | (U-4) | (Ae-1) | (P-1) | (U-1) |
| | Outer layer | Single layer | Single layer | Single layer | (U-1) | (E-1) | (E-1) | (E-1) | (E-1) | (E-1) | (Ae-1) |
| Elasticity | | A | C | C | A | A | A | A | A | B | B |
| Bending durability | | C | B | C | AA | AA | AA | AA | AA | B | AA |
| Heat cycle resistance | | A | A | C | AA | AA | AA | AA | AA | AA | AA |

TABLE 3-2

| | | | Ex. 51 |
|---|---|---|---|
| Porous layer | | Type | (L-4) |
| | | Average pore size | 1.2 μm |
| | | Primer layer | (S-1) |
| Polymer cover layer | | Inner layer | (U-1) |
| | | Outer layer | (P-1) |
| | Elasticity | | B |
| | Bending durability | | B |
| | Heat cycle resistance | | A |

| | | Com. 1 | Com. 2 | Com. 3 | Com. 4 | Com. 5 | Com. 6 | Com. 7 | Com. 8 |
|---|---|---|---|---|---|---|---|---|---|
| Interlayer | Type | — | (R-1) | (R-2) | (L-4) | (L-4) | — | — | — |
| | Average pore size | | *1 | *1 | 1.2 μm | 1.2 μm | | | |
| Primer layer | | (S-1) | (S-1) | (S-1) | — | (S-1) | (A-1) | (Z-1) | (T-1) |
| Polymer cover layer | Inner layer | (U-1) | (U-1) | (U-1) | (U-1) | (F-1) Single layer | (U-1) | (U-1) | (U-1) |
| | Outer layer | (E-1) | (E-1) | (E-1) | (E-1) | | (E-1) | (E-1) | (E-1) |
| Elasticity | | B | C | C | B | D | C | C | C |
| Bending durability | | D | D | D | D | D | D | D | D |
| Heat cycle resistance | | D | D | D | D | D | D | D | D |

*1 Pores are not observed.

29

30

Notes in Table 3

The abbreviations shown in the above tables are as follows.

Ex.: Example

Com.: Comparative Example

Silane Coupling Agents (S-1):

N-2-(Aminoethyl)-3-aminopropylmethyldimethoxysilane (trade name: KBM-603, manufactured by Shin-Etsu Chemical Co., Ltd.)

(S-2):

3-Aminopropyltrimethoxysilane (trade name: KBM-903, manufactured by Shin-Etsu Chemical Co., Ltd.)

(S-3):

N-Methylaminopropyltrimethoxysilane (reagent)

(S-4):

3-Ureidopropyltrialkoxysilane (trade name: KBE-585, manufactured by Shin-Etsu Chemical Co., Ltd.)

(S-5):

N-Phenyl-3-aminopropyltrimethoxysilane (trade name: KBM-573, manufactured by Shin-Etsu Chemical Co., Ltd.)

(S-6):

3-Trimethoxysilylpropylsuccinic anhydride (trade name: X-12-967C, manufactured by Shin-Etsu Chemical Co., Ltd.)

(S-7):

(3-Methacryloxypropyl)trimethoxysilane (trade name: KBM-503, manufactured by Shin-Etsu Chemical Co., Ltd.)

(S-8):

3-Glycidoxypropyltrimethoxysilane (trade name: KBM-403, manufactured by Shin-Etsu Chemical Co., Ltd.)

(S-9):

3-Mercaptopropyltrimethoxysilane (trade name: KBM-803, manufactured by Shin-Etsu Chemical Co., Ltd.)

Aluminum Coupling Agents (A-1):

Aluminum sec-butoxide (trade name: ASBD, manufactured by Kawaken Fine Chemicals Co., Ltd.)

(A-2):

Aluminum trisacetylacetonate (trade name: ORGATIX AL-3100, manufactured by Matsumoto Fine Chemical Co., Ltd.)

(A-3):

Aluminum bisethylacetoacetate monoacetylacetonate (trade name: ORGATIX AL-3200, manufactured by Matsumoto Fine Chemical Co., Ltd.)

(A-4):

Aluminum trisethylacetoacetate (trade name: ORGATIX AL-3215, manufactured by Matsumoto Fine Chemical Co., Ltd.)

(A-5):

Aluminum octadecylacetoacetate diisopropylate (trade name: PLENACT AL-M, manufactured by Ajinomoto Fine-Techno Co., Inc.)

Zirconium Coupling Agents (Z-1):

Zirconium tetra-n-propoxide (trade name: ORGATIX ZA-45, manufactured by Matsumoto Fine Chemical Co., Ltd.)

(Z-2):

Zirconium tetra-n-butoxide (trade name: ORGATIX ZA-65, manufactured by Matsumoto Fine Chemical Co., Ltd.)

(Z-3):

Zirconium tetraacetylacetonate (trade name: ORGATIX ZC-150, manufactured by Matsumoto Fine Chemical Co., Ltd.)

(Z-4):

Zirconium lactate ammonium salt (trade name: ORGATIX ZC-300, manufactured by Matsumoto Fine Chemical Co., Ltd.)

(Z-5):

Zirconium tri-n-butoxide stearate (trade name: ORGATIX ZC-320, manufactured by Matsumoto Fine Chemical Co., Ltd.)

Titanium Coupling Agents (T-1):

Tetra-n-butyl titanate (trade name: ORGATIX TA-21, manufactured by Matsumoto Fine Chemical Co., Ltd.)

(T-2):

n-Butyl titanate dimer (trade name: ORGATIX TA-23, manufactured by Matsumoto Fine Chemical Co., Ltd.)

(T-3):

Isopropyl triisostearoyl titanate (trade name: PLENACT TTS, manufactured by Ajinomoto Fine-Techno Co., Inc.)

(T-4):

Dioctyl bis(ditridecyl)phosphate titanate (trade name: PLENACT 46B, manufactured by Ajinomoto Fine-Techno Co., Inc.)

(T-5):

Diisopropyl bis(dioctyl pyrophosphate) titanate (trade name: PLENACT 38S, manufactured by Ajinomoto Fine-Techno Co., Inc.)

(U-1):

Polyether polyurethane elastomer (trade name: PANDEX T-8185, manufactured by DIC Corporation)

(U-2):

Polyether polyurethane elastomer (trade name: Miractran E380, manufactured by Nippon Polyurethane Industry Co., Ltd.)

(U-3):

Polyester polyurethane elastomer (trade name: Miractran E480, manufactured by Nippon Polyurethane Industry Co., Ltd.)

(U-4):

Polycarbonate polyurethane elastomer (trade name: PANDEX T-9280, manufactured by DIC Corporation)

(E-1):

Polyester elastomer (trade name: PELPRENE P-40B, manufactured by Toyobo Co., Ltd.)

(Ae-1):

Polyamide elastomer (trade name: Pebax 4533, manufactured by Arkema Inc.)

(P-1):

Polyolefin elastomer: Zelas MC707 (trade name), manufactured by Mitsubishi Chemical Corporation (F-1):

Fluorine-containing elastomer: DAI-EL T-530 (trade name), manufactured by Daikin Industries, Ltd.

The above tables show the following.

The flexible tubes of Comparative Examples 1 and 6 to 8, which do not have the porous layer defined in the present invention, are inferior in adhesiveness and heat resistance even though they have the primer layer.

The flexible tube of Comparative Example 2 has an epoxy resin layer between the flexible-tube base and the primer layer. However, since the epoxy resin layer is not porous, the flexible tube is inferior in adhesiveness and heat resistance. Similarly, the flexible tube of Comparative Example 3, which has a non-porous silica layer between the flexible-tube base and the primer layer, is inferior in adhesiveness and heat resistance.

The flexible tube of Comparative Example 4 has the porous layer defined in the present invention but does not have the primer layer defined in the present invention. This flexible tube is inferior in adhesiveness and heat resistance.

The flexible tube of Comparative Example 5 has a fluorine-containing elastomer layer serving as a polymer cover layer. Specifically, the flexible tube does not have the polymer cover layer defined in the present invention. This flexible tube is inferior in all of elasticity, adhesiveness, and heat resistance.

In contrast, the flexible tubes of Examples 1 to 51 according to the present invention have sufficient elasticity and good adhesiveness and further have good heat resistance.

REFERENCE SIGNS LIST 2 electronic endoscope (endoscope)
3 insertion section
   3a flexible tube
   3b angle portion
   3c tip portion
5 main-body operation section
6 universal cord
11 spiral tube
   11a metal strip
12 tubular mesh member
13 cap
14 flexible-tube base
   14a distal end side
   14b proximal end side
15 polymer cover layer
16 topcoat layer
17 inner layer
18 outer layer
X angle portion 3b side (soft)
Y main-body operation section 5 side (hard)
20 continuous molding machine (production apparatus)
21, 22 extrusion unit
   21a screw
   22a screw
23 head unit
24 cooling unit
25 transport unit
26 control unit
28 feed drum
29 take-up drum
30 joint member
31 connected flexible-tube base
32 nipple
33 die
34 support
35, 36 gate
37 molding passage
38 polymer passage
39 first polymer material (soft polymer)
40 second polymer material (hard polymer)

What is claimed is:

1. A flexible tube for an endoscope, the flexible tube comprising:
a flexible-tube base containing metal as a constituent material;
a porous layer on the flexible-tube base;
a primer layer on the porous layer; and
a polymer cover layer on the primer layer, wherein the polymer cover layer includes at least one compound of a polyamide, a polyester, a polyurethane, or a polyolefin on a side in contact with the primer layer,
wherein the porous layer includes crosslinked products of epoxy resins.

2. The flexible tube for an endoscope according to claim 1,
wherein
the porous layer has an average pore size of 50 nm to 100 μm.

3. The flexible tube for an endoscope according to claim 1, wherein the primer layer includes at least one of a silane coupling agent, a titanium coupling agent, a zirconium coupling agent, or an aluminum coupling agent.

4. The flexible tube for an endoscope according to claim 1, wherein the primer layer includes a silane coupling agent.

5. The flexible tube for an endoscope according to claim 1, wherein the primer layer includes an amino silane coupling agent.

6. The flexible tube for an endoscope according to claim 1, wherein the metal that constitutes the flexible-tube base is stainless steel.

7. The flexible tube for an endoscope according to claim 1, wherein the metal that constitutes the flexible-tube base has a passivation film on a surface of the metal.

8. The flexible tube for an endoscope according to claim 1, wherein the polymer cover layer has a single-layer structure or a multilayer structure and includes at least one compound of a polyamide, a polyester, a polyurethane, or a polyolefin in a layer in contact with the primer layer.

9. The flexible tube for an endoscope according to claim 1,
wherein the polymer cover layer has a two-layer structure, and
a proportion of a thickness of an inner layer to a thickness of an outer layer of the two-layer structure changes in a gradient manner in an axial direction of the flexible-tube base.

10. The flexible tube for an endoscope according to claim 9, wherein the proportion of the thickness of the inner layer to the thickness of the outer layer is inner layer:outer layer=95:5 to 60:40 at one end of the flexible tube for an endoscope and is inner layer:outer layer=5:95 to 40:60 at the other end.

11. An endoscopic medical device comprising the flexible tube for an endoscope according to claim 1.

12. A method for producing an endoscopic medical device, the method comprising incorporating, into an insertion section of an endoscopic medical device, the flexible tube for an endoscope according to claim 1.

13. A method for producing a flexible tube for an endoscope, the method comprising:
forming, on a flexible-tube base containing metal as a constituent material, a porous layer having an average pore size of 50 nm to 100 μm;
forming a primer layer on the porous layer; and
forming a polymer cover layer on the primer layer,
wherein the polymer cover layer includes at least one compound of a polyamide, a polyester, a polyurethane, or a polyolefin on a side in contact with the primer layer, and
wherein the porous layer includes crosslinked products of epoxy resins.

14. A method for producing an endoscopic medical device, the method comprising incorporating, into an insertion section of an endoscopic medical device, a flexible tube for an endoscope obtained by the method for producing a flexible tube for an endoscope according to claim 13.

\* \* \* \* \*